United States Patent
Andrus et al.

(10) Patent No.: US 7,405,650 B2
(45) Date of Patent: Jul. 29, 2008

(54) DEVICE WITH IMPROVED SERIAL COMMUNICATION

(75) Inventors: Jeremy C. Andrus, Zeeland, MI (US); Timothy R. Friend, Grandville, MI (US); Jon H. Bechtel, Holland, MI (US); Robert R. Turnbull, Holland, MI (US)

(73) Assignee: Gentex Corporation, Zeeland, MI (US)

( * ) Notice: Subject to any disclaimer, the term of this patent is extended or adjusted under 35 U.S.C. 154(b) by 417 days.

(21) Appl. No.: 11/017,128

(22) Filed: Dec. 20, 2004

(65) Prior Publication Data

US 2005/0135465 A1 Jun. 23, 2005

Related U.S. Application Data

(60) Provisional application No. 60/531,484, filed on Dec. 19, 2003.

(51) Int. Cl.
*B60R 25/10* (2006.01)

(52) U.S. Cl. .................. 340/426.16; 340/462

(58) Field of Classification Search ............ 340/426.16, 340/459, 460, 461, 462, 517; 375/220, 222, 375/354, 360, 376; 370/503, 465; 327/113, 327/114; 341/143, 155; 701/36, 48; 708/490, 708/231

See application file for complete search history.

(56) References Cited

U.S. PATENT DOCUMENTS

| | | | | |
|---|---|---|---|---|
| 5,359,631 A * | 10/1994 | Behrens et al. | ............. | 375/376 |
| 5,534,848 A * | 7/1996 | Steele et al. | ................ | 340/517 |
| 5,878,061 A * | 3/1999 | Hauck et al. | ................ | 714/800 |
| 5,964,825 A * | 10/1999 | Seshan et al. | ............... | 708/490 |
| 6,028,903 A * | 2/2000 | Drost et al. | ................. | 375/360 |
| 6,140,952 A * | 10/2000 | Gaboury | ..................... | 341/143 |
| 6,144,291 A * | 11/2000 | Odinak et al. | .......... | 340/310.12 |
| 6,377,640 B2 * | 4/2002 | Trans | ......................... | 375/354 |
| 6,501,307 B1 * | 12/2002 | Yen | ............................ | 327/113 |
| 6,611,537 B1 * | 8/2003 | Edens et al. | ................ | 370/503 |
| 6,907,331 B2 * | 6/2005 | Paquet | ......................... | 701/36 |
| 6,954,491 B1 * | 10/2005 | Kim et al. | ................... | 375/220 |

* cited by examiner

*Primary Examiner*—Van T. Trieu
(74) *Attorney, Agent, or Firm*—James E. Shultz, Jr.

(57) ABSTRACT

The present invention relates to various improvements to digital communications and various applications of the improved digital communications.

7 Claims, 11 Drawing Sheets

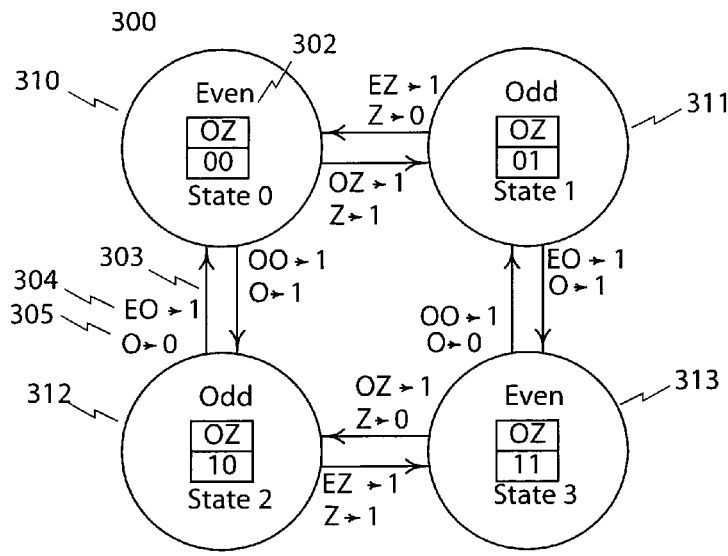

```
In state diagram, let EO = ~clk & en_o_e
In state diagram, let EZ = ~clk & en_z_e        306
In state diagram, let OO =  clk & en_o_o
In state diagram, let OZ =  clk & en_z_o
```
                                                                    307

```
assign soout = (EO &  zout) | (OO & ~zout);
assign roout = (EO & ~zout) | (OO &  zout);
assign szout = (EZ &  oout) | (OZ & ~oout);
assign rzout = (EZ & ~oout) | (OZ &  oout);
assign oout  = ~(noout | roout | clr);
assign noout = ~( oout | soout);
assign zout  = ~(nzout | rzout);
assign nzout = ~( zout | szout | clr);
```

If the odd bit is to automatically follow the even so that trans-
mition is in close spaced even-odd pairs, then ood may be used to
signify the value of the odd bit of the pair and en_o_o may be
replaced by the value ood of the odd bit and en_z_o may be replaced
by the value ~ood which is the complemented value of the odd bit.

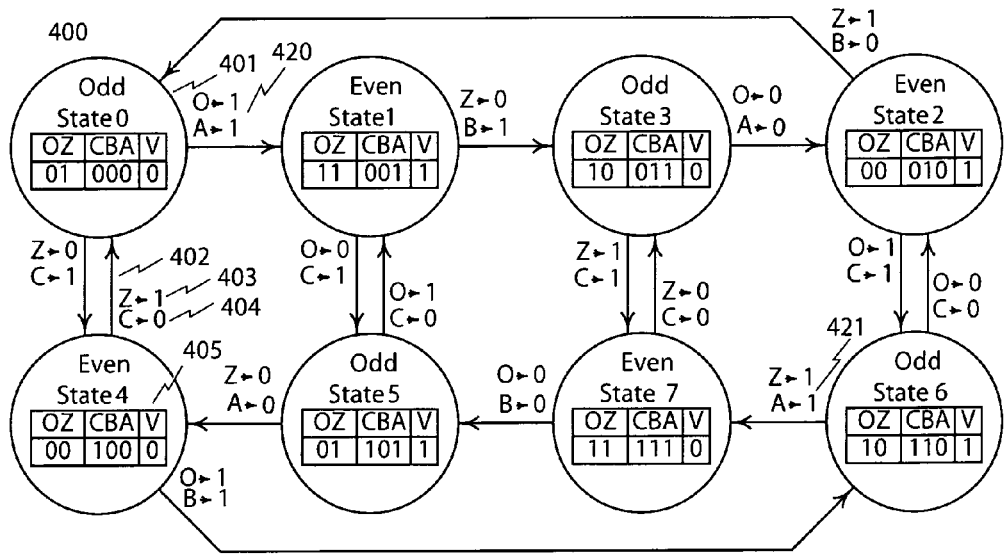

```
assign nsfa = ~(ssfa | sfa);
assign sfa  = ~(rsfa | nsfa | clr);
assign nsfb = ~(ssfb | sfb);
assign sfb  = ~(rsfb | nsfb | clr);
assign nsfc = ~(ssfc | sfc);
assign sfc  = ~(rsfc | nsfc | clr);
```
406

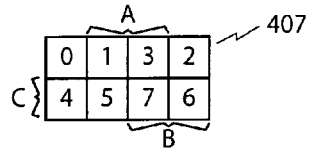
407

```
assign ssfa = (~sfc & ~sfb & ~sfa &  oin) | ( sfc &  sfb & ~sfa &  zin);
assign rsfa = (~sfc &  sfb &  sfa & ~oin) | ( sfc & ~sfb &  sfa & ~zin);
assign ssfb = (~sfc & ~sfb &  sfa & ~zin) | ( sfc & ~sfb & ~sfa &  oin);
assign rsfb = (~sfc &  sfb & ~sfa &  zin) | ( sfc &  sfb &  sfa & ~oin);
assign ssfc = (~sfc &  sfb & ~sfa &  oin) | (~sfc &  sfb & sfa &  zin) |
              (~sfc & ~sfb &  sfa & ~oin) | (~sfc & ~sfb & ~sfa & ~zin);
assign rsfc = ( sfc & ~sfb & ~sfa &  zin) | ( sfc & ~sfb &  sfa &  oin) |
              ( sfc &  sfb &  sfa & ~zin) | ( sfc &  sfb & ~sfa & ~oin);
```
408

```
assign oclk = ~( sfc ^ sfb ^ sfa);
```
409

```
assign npodo = ~( sfc &  sfb & ~sfa |  sfc & ~sfb &  sfa | podo);
assign podo  = ~(~sfc & ~sfb & ~sfa | ~sfc &  sfb &  sfa | npodo);
assign nevo  = ~(~sfc & ~sfb &  sfa | ~sfc &  sfb & ~sfa | evo);
assign evo   = ~( sfc &  sfb &  sfa |  sfc & ~sfb & ~sfa | nevo);
```
410

```
ffdc_1 odof   (.c(oclk), .clr(clr), .d(podo),  .q(odo));
ffdc  pevodf  (.c(oclk), .clr(clr), .d(evo),   .q(pevod));
ffdc_1 evodf  (.c(oclk), .clr(clr), .d(pevod), .q(evod));
```
411

Fig. 4

DEVICE WITH IMPROVED SERIAL COMMUNICATION

CROSS REFERENCE TO RELATED APPLICATIONS

This application claims the benefit under 35 U.S.C. §119 (e) of U.S. Provisional Patent Application Ser. No. 60/531,484, entitled "ONE-ZERO SERIAL COMMUNICATION," which was filed Dec. 19, 2003, and which is hereby incorporated herein by reference in its entirety.

BACKGROUND OF THE INVENTION

The present invention relates to various improvements to digital communications and various applications of the improved digital communications.

BRIEF DESCRIPTION OF THE FIGURES

FIG. 3 depicts a state diagram of a sequenced to generate a one zero data stream;

FIG. 4 depicts a sequence state diagram of a sequencer which accepts signals with a one-zero serial code and generates a clock and data stream;

DETAIL DESCRIPTION

Various embodiments of the present invention are applicable to a host of digital data transmissions. The improved digital communications described herein are applicable for text, numerical, video and audio transmissions. The present invention may be used for residential, commercial, industrial and vehicular applications where it is desirable to transmit digital information between associated devices.

In at least one embodiment, the present invention is employed in test equipment used in manufacturing vehicular related equipment. In many of the embodiments, the digital communications is described with regard to an interface unit and a remote unit.

In at least one embodiment, the present invention is employed in vehicular related equipment control. The present invention may be used in vehicle exterior light control systems using an image sensor and image processing system as described in commonly assigned U.S. Pat. Nos. 5,837,994, 5,990,469, 6,008,486, 6,130,448, 6,130,421, 6,049,171, 6,465,963, 6,403,942, 6,587,573, 6,611,610, 6,621,616, 6,631,316 and U.S. patent application Ser. Nos. 10/208,142, 09/799,310, 60/404,879, 60/394,583, 10/235,476, 10/783,431, 10/777,468, 09/800,460 and 60/590,736; the disclosures of which are incorporated herein in their entireties by reference. The present invention may be used in moisture sensor and vehicle controls as described in commonly assigned U.S. Pat. Nos. 5,923,027 and 6,617,564 and U.S. patent application Ser. Nos. 09/970,728 and 60/472,017; the disclosures of which are incorporated herein in their entireties by reference.

Figure 1:
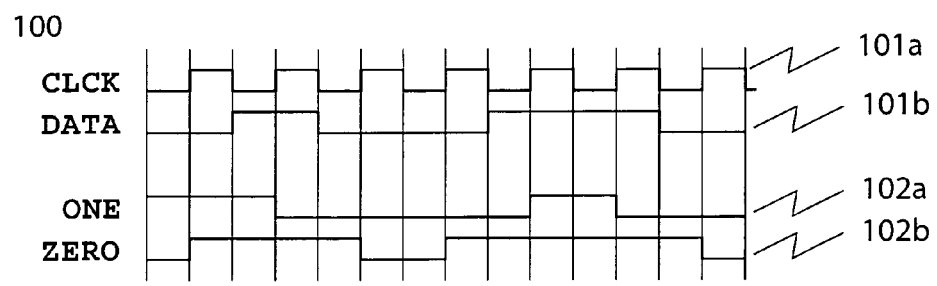
FIG. 1 depicts two methods of decoding a seven bit data stream.
Figure 2:
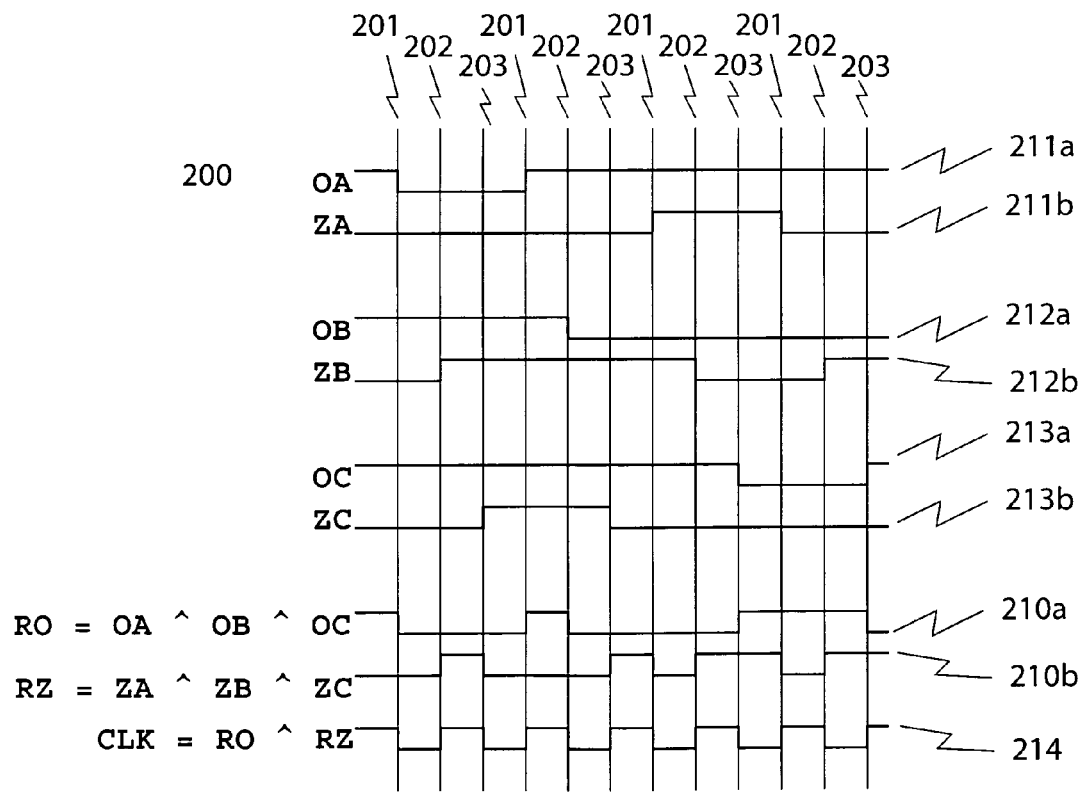
FIG. 2 depicts three signal pairs with one-zero encoding and a multiplexed resultant signal pair.

Referring now to FIG. 1, two data trace pairs 100 depict two methods to encode the same seven bit serial data stream. Each method uses a pair of binary valued signal lines. The first pair of data traces 101a and 101b depict a conventional clock data encoding. The second pair of traces 102a and 102b depict a novel one/zero encoding which is used in this invention. Data 101a depicts a digital clock signal and data trace 101b depicts an associated data signal. The data signal is sampled at each rising edge of the clock to obtain a seven bit serialized data string. In the alternate encoding of the same seven bit serialized data stream depicted by data traces 102a and 102b, a one is encoded as single signal transition on data line 102a and a zero is encoded as a single signal transition on data line 102b. For convenience line 102a is referred to as the one signal or signal line and line 102b is referred to as the zero signal or signal line. In the clock/data transmission, there are 18 signal transitions as opposed to 7 signal transitions with the one/zero encoding. The maximum transition rate for the one/zero encoding is one half of the transition rate for the clock signal and there are fewer than half as many total transitions. The one/zero transmission scheme requires a lower bandwidth and generates less radiated interference than the clock data transmission. The fact that the one/zero transmission encoding has exactly one transition per bit is used advantageously in an asynchronous receiver circuit which translates the one/zero bit stream to its binary equivalent. The encoding also has the advantage that interleaved sets of values may be individually encoded into the one/zero format and then merged together into a single one/zero encoded stream as illustrated by the example of FIG. 2. It should be understood that any of the concepts of the specific embodiments described herein may be extrapolated and applied to eight-bit, ten-bit, sixteen-bit, thirty-two-bit, sixty-four-bit, etc. serial communication schemes.

Referring to FIG. 2, three signal pairs with one/zero encoding are depicted in data trace group 200 along with a fourth one/zero encoded pair which has three times the transmission rate and which combines the data from the first three pairs. Vertical lines 201, 202, and 203 are preferably approximately equally spaced along the time line and are repeated in a sequence 201, 202, 203, 201, 202, 203 etc. Transitions for the one signal 211a and the zero signal 211b occur at the times depicted by vertical lines 201. Likewise, transitions for the one signal 212a and the zero signal 212b occur at the times depicted by vertical lines 202 and transitions for the one signal 213a and the zero signal 213b occur at the times depicted by vertical lines 203. With each of the one/zero signal pairs, there is only one transition at a time, and since transitions for each of the three pair are skewed or sequenced in time, there is only one transition for the combined set of three signal pairs at each of the vertical time lines in the combined set of all of the time lines in 201, 202 and 203. The fourth one/zero signal pair has a resultant one signal RO, 210a, which is generated by exclusive-or'ing the one lines 211a, 212a and 213a and a resultant zero signal RZ, 210b, which is generated by exclusive-or'ing the zero lines 211b, 212*b* and 213*b*. In principle any number of one/zero encoded signal pairs may be multiplexed or merged into a higher bit rate one/zero encoded pair using this technique. Three one/zero signal pairs were chosen to illustrate the general nature of this technique. Multiplexing of two signal pairs is of particular practical importance because transitions for a signal generated directly by states of a synchronous sequencer normally do not have more then one transition per clock but the transition may occur at the positive clock edge if positive edge triggered flip-flops are used in the sequencer or at the negative clock edge if negative edge triggered flip-flops are used in a sequencer. With the multiplexing technique depicted in FIG. 2 but altered to multiplex two instead of three one/zero encoded signal pairs, the even numbered bits in a data stream may, for example, be generated by a sequencer which transitions on the positive edge of the system clock and the odd numbered bits in a data stream may, for example, be generated by a sequencer which transitions on the negative edge of the system clock. The resulting pair of one signals may be exclusive-or'ed together to form the one signal for the complete multiplexed data stream and; likewise, the resulting pair of zero signals may be exclusive-or'ed together to form the zero signal for the complete multiplexed data stream. In this way, a serial data stream which has a bit rate which is twice the frequency of the system clock may be generated. In association with FIG. 3, an alternate method which utilizes asynchronous logic will be described.

For each bit which is serially transmitted, there is exactly one signal state change which occurs for either the zero serial data channel or the one serial data channel. Thus, an exclusive-or of the one and zero serial data signals will change state once with transmission of each successive bit. This is a very effective way to generate a reconstructed clock signal having an edge at each bit transmission so that the frequency of the exclusive-or signal is half of the transmitted or received bit rate. For designs for which a continuous stream of bits is transmitted, this may be a convenient way of generating a clock signal, particularly since it is synchronized with the incoming bit stream. It is still convenient as a data recovery clock even when data transmission is not continuous. When a derived or recovered clock is used to input the data, there is normally a pipelined sequence so that the clock edge for which data is stored is typically derived in the clock recovery process from, for example, the first, second or third bit following the one being stored. It is advantageous to establish a data transmission protocol which includes bits whose values do not need to be read and to insert or include these bits in the data stream so that they are transmitted immediately prior to pauses or break points in the data transmission sequence. With these bits whose values do not need to be read at the end of the sequence, the data bits transmitted just before these bits may be read in timely fashion by using clock pulses generated by receipt of the added bits at the end of the sequence. Without these added bits, specialized provisions would have to be made in the receive logic to read the bits which were being processed when the recovered clock sequence ended. The value and/or number of added bits may serve an added function to bring the one and/or zero transmission lines to a desired state. This is especially useful just prior to switching direction for a bidirectional bus.

Two general problems are encountered and there is synergy in their solution. To transmit or receive data streams at bit rates which are up to two times the system clock frequency, it is necessary to decode two bits per clock cycle. With each bit that is transmitted, the two signal lines alternate between matching each other and mismatching each other in a repeating cyclic pattern. This cyclic pattern is an artifact of the one/zero encoding scheme which can cause difficulty. In order to circumvent this difficulty and to provide for handling two bits per clock cycle, it has been found convenient to keep track of the even and odd bit status for each transmitted and received bit. For these discussions, bits for which the state's of the one and the zero lines match each other just following transmission of the bit are referred to as even bits. For the alternate bits, the states of the one and the zero lines mismatch each other just following transmission of the bit. For discussion, these bits are called odd bits. It is convenient to send and receive even/odd or alternatively odd/even bit pairs or bit groups. Since the pairs may be transmitted or received as a pair of two per clock cycle, the bit pairing is a good way to organize the sending and/or receiving of the bits so that a bit pair may be handled with each clock cycle. In this way, data rates of as much as twice the system clock frequency may be handled without difficulty.

The pairing or grouping may also be used to control the match/mismatch state (exclusive-or value) of the one and zero data lines during pauses in the transmission. When data is normally handled as packets which may simply be pairs of bits, bytes, or other bit lengths for which the even/odd status is accounted for, the transmission can be arranged so that normal pauses in the transmission occur when the one and zero data lines either match each other (even state) or alternatively mismatch each other (odd state). Then, special pauses or longer dwell times which are not part of the routine transmission pattern on the alternate odd/even bit boundary may be used to signal special events in the transmission sequence. For example, the start or end of an instruction sequence may be signalled in such a way. With such a protocol, longer than normal duration of intervals for which the one and zero signal lines remain in the alternate matching state are measured and detected and used to signal that a particular action is to be taken. Such an exception to the normal transmission pattern is frequently referred to as a code violation. This particular type of code violation is new to the inventors. An example of a code violation for a common prior art pulse width modulated transmission protocol is the use of a pulse width which exceeds the longest pulse width used for encoding a normal data bit. Such a violation is used in prior art systems to signal the end of a transmitted data word.

Another property of the transmitted waveforms which may be used for checking data integrity is that the state of the one line is an indication of the parity of the ones which have been transmitted and the state of the zero line is an indication of the parity of the zeros which have been transmitted. This is so because the one line state toggles exactly once for each one transmitted and the state of the zero line toggles exactly once for each zero which is transmitted. The one zero encoding has the property that the transmission of a bit value is effected by a level transition on a transmission line which is associated with the value. The facts that the encoding is transition rather than level specific and that the transition indicates both the occurrence of the transmitted bit (data clocks) and the value (one for one line transition and zero for zero line transition) lead to the ability to multiplex interleaved data streams using exclusive-or functions as illustrated in FIG. 2. The properties above which are of particular value in handling data streams whose bit rates exceed the system clock frequency are not shared by the Data-Strobe (DS) coding used in the IEEE 1394-1995 and 1394a specifications. DS encoding and one-zero encoding share the properties that data is transmitted over a pair of signaling channels and that these is exactly one transition for each bit transmitted i.e. there is a transition on one or the other but not both of the signaling channels. In at least one embodiment of the present invention, an apparatus is provided comprising an interface unit, a digital serial communication link comprising an electronic signal comprising only one signal state change per transmitted bit with encoding that is transition specific and a remote unit in communication with the interface unit via the digital serial communications link. The fact that the encoding is transition specific in this embodiment of the present invention is a distinguishing feature when compared with known DS encoding.

Turning now to FIG. 3, item 300 is a state diagram having four states. Each of the four states is represented by a circle, 310, 311, 312 or 313. In a preferred implementation, two sequencer state flip-flops are used. The first is called the O flip-flop and is preferably configured to be set to the state to which the one or O output line should be driven.

The second is called the Z flip-flop and is preferably configured to be set to the state to which the zero or Z output line should be driven. In state 0 (310) the one and zero outputs are both driven to the zero level and in state 3 (313) the one and zero states are both driven to the one level. These are referred to as the even states which are selected to be driven by the even numbered bits in the bit stream. In state 1 (311) the one or O output is driven to the zero level and the zero or Z output is driven to the one level, and in state 2 (312) the one or O output is driven to the one level and the zero or Z output is driven to the zero level. These are referred to as the odd states which are selected to be driven by the odd numbered bits in the bit stream. In state diagram 300, there are eight lines of which 303 is one which indicates possible transitions between various sequencer states. Each has an arrow which indicates that the transition is from one state to another along the path of the line in the direction indicated by the arrow. Each arrow has two associated designations. For example arrow 303 has EO followed by an arrow and a 1. EO is an input to the sequencer logic which is asserted to command the sequencer to output an even one. EZ is an input to the sequencer logic which is asserted to command the sequencer to output an even zero. OO is an input to the sequencer logic which is asserted to command the sequencer to output an odd one. OZ is an input to the sequencer logic which is asserted to command the sequencer to output an odd zero. An associated O (such as 305) followed by an arrow and a 1 or a 0 indicates that the one state flip-flop and the associated one output are to be driven, respectively, to 1 or to 0 to achieve the appropriate state transmission in response to the assertion of the indicated one of the EO or OO send bit commands. Similarly an associated Z followed by an arrow and a 1 or a 0 indicates that the zero state flip-flop and the associated zero output are to be driven, respectively, to 1 or to 0 to achieve the appropriate state transmission in response to the assertion of the indicated one of the EZ or OZ send bit commands. The sequencer control logic responds to the input commands and to the current sequencer state in combination to determine the controlling action required to cause the desired state transition or to maintain the present state. For the sequencer as it is shown, only one state flip-flop changes value for any one of the eight allowed transitions. This is a desirable condition for an asynchronous sequencer design because simultaneous transitions in the state flip-flops or in the controlling commands EZ, EO, OZ, or OO can easily lead to ambiguous race conditions in the controlling logic which may cause the sequencer to transition to incorrect or even invalid states. This is one more point at which having exactly one output transition per bit transmitted has beneficial implications for the associated control logic. The benefit is even more direct for the receiver of FIG. 4. Note that all possible transitions are from an even state to an odd state or vise versa. When the bit rate is up to two times higher than the clock frequency, the sequencer logic is preferably asynchronous. The sequencer is designed so that the EZ or EO commands should be asserted when the sequencer is in an odd state and the OO or OZ commands should be asserted when the sequencer is in an even state. Block 306 indicates a way of generating EO and EZ by anding the complemented clock (~clk) with en_o_e or en_z_e, respectively, where en_o_e or en_z_e should be asserted for one clock period following a positive clock edge. Block 306 also indicates a way of generating OO and OZ by anding the clock (clk) with en_o_o or en_z_o, respectively, where en_o_o or en_z_o should be asserted for one clock period following a negative clock edge. It is preferable in this part of the design to assure that unwanted glitches which may cause malfunction of the control logic are not generated. Use of a low skew network for clk as is common in synchronous design is helpful for this portion of the design phase. Most likely, the logic of block 306 is a point of interface between synchronous and asynchronous elements in the control logic. The verilog style statements in block 307 provides an example for a specific fragmentary design to implement a circuit which may be operated in accordance with the requirements of sequence state diagram 300. Block 307 uses the signals which are defined in block 306 which utilizes a system clock to generate the command signals EZ, EO, OZ, or OO. A clear, clr, is optional and may, for example, be used to bring the sequencer to a known state at power up. A flip-flop to provide the O state function is formed by cross connected nor flip-flops having output oout corresponding to O and noout corresponding to ~O. Logic expressions for soout and roout provide the respective set and reset functions for this flip-flop and function to control the state of the oout, O, flip-flop in accordance with the state transitions indicated in state diagram 300. In these equations and discussions the verilog symbols ~, |, & and ^ are used, respectively, to denote complement, bitwise or, bitwise and, and bitwise exclusive-or. Likewise, a flip-flop to provide the Z state function is formed by cross connected nor flip-flops having output zout corresponding to Z and nzout corresponding to ~Z. Logic expressions for szout and rzout provide the respective set and reset functions for this flip-flop and function to control the state of the zout, Z, flip-flop in accordance with the state transitions indicated in state diagram 300.

Referring now to FIG. 4, sequence state diagram 400 details the states of a sequencer that accepts signals with a one/zero serial code and generates a clock and data stream. The states that the sequencer assumes indicate the values of the received data bits and their odd/even status. 401 is a representative state. Transitions on the O input cause transitions to states that indicate that a 1 was received and transitions on the Z input cause transitions to states that indicates that a 0 was received. Additionally, transitions are to states which correctly indicate the even (matching) or odd (mismatching) values of the O and Z inputs. A table in each state lists the value of the O input under O, the value of the Z input under Z, the value of state flip-flop sfc under C, the value state flip-flop sfb under B, the value of state flip-flop sfa under A, and the value of the data bit which was just received under V. The odd and even classification of the state is also listed as odd when the values of the O and Z inputs do not match each other and as even when the values of the O and Z inputs do match each other. The state number designations have been assigned so that they agree with the binary value of state flip-flops C, B, and A with C taken as the most significant bit and A taken as the least significant bit. The states are also arranged to agree with their relative locations as they appear in Karnaugh map 407. A transition on the one (O) or the zero (Z) input line triggers the transition to a state for which the associated value of V is equal to the value of the data bit which was just received. The one/zero serial transmission protocol has the property that only one transition takes place for each bit that is transmitted. The sequencer state transitions are further arranged so that for every valid state transition exactly one of the state flip-flop values A, B, or C changes. The sequencer for which only one input condition changes at a time and for which only one state flip-flop value changes at a time can be designed to operate asynchronously without having race conditions between simultaneously changing inputs or state variables to present a serious timing problem. Each valid transition is represented by an arrow of which 402 is representative. The transition is between the states connected by the arrow and occurs in the direction indicated by the arrow head. An indicated input value transition of which 403 is representative indicates the input O or Z which has just changed to trigger the transition and an arrow to a 1 or 0 value indicates whether the transition is to 1 or to 0, respectively. Inspection of the values of the O and the Z inputs for each state and the possible transitions in these input values along with the resulting state changes and the data bit value V indicated for the change will verify that the state diagram accomplishes the desired conversion of the O and Z, one/zero code, transitions to appropriate data bit value indications V. The expression 404 indicates that state flip-flop C is driven to zero to effect the state change indicated by arrow 402. For each of the state changes, the state flip-flop A, B, or C which is changed to effect the transition is listed with an arrow which points to the 1 or 0 value to which the state flip-flop is driven to cause the desired transition change.

Blocks 406 through 411 contain small portions of Verilog code that indicates how portions of the sequencer which operates generally in accordance with the sequencer 400 may be implemented. In block 406, three asynchronous set reset flip-flops are instantiated using cross coupled pairs of nor gates. Flip-flop sfa is described by the first equation which defines a nor gate with output sfa for the sfa output and the second equation which defines a nor gate with output nsfa for the complemented sfa output. An optional clear input, clr, may be used and is generally intended to be used either at power up or as a hard reset. The ssfa input is asserted to set the sfa flip-flop and the rsfa input is asserted to reset the sfa flip-flop. The other two pairs of equations in block 406 define the sfb and sfc flip-flops. These equations parallel those for sfa with the letter a being replaced, respectively, by the letter b or the letter c.

Block 408 contains the Verilog expressions defining the set and reset functions which control the flip-flops of block 406 and which in turn control the state transitions in sequence diagram 400. In some detail, the first expression in block 408 defines the combinatorial logic block with output ssfa. ssfa is asserted to set state flip-flop sfa. Inspection of the sequence diagram 400 indicates that the transition at 420 and the transition at 421 are the two for which the flip-flop sfa is set. At 420, sfa is set when the sequencer is in state 0 (~sfc & ~sfb & ~sfa) and O is asserted (oin) so the total expression to assert ssfa to cause flip-flop sfa to be set and to in turn cause the transition at 420 to happen is (~sfc & ~sfb & ~sfa & oin). In a similar manner the total expression to cause flip-flop sfa to be set and to in turn cause the transition 421 to happen is (sfc & sfb & ~sfa & zin). Since these are the only two transitions for which flip-flop sfa is to be set, the total expression to set sfa is the or of the above two expressions which is ssfa=(~sfc & ~sfb & ~sfa & oin)|(sfc & sfb & ~sfa & zin). Inspection of the transitions in state diagram 400 indicates that there are also two transitions for which rsfa is asserted to reset flip-flop sfa and similarly two transitions each where the flip-flop sfb is set or reset. There are four transitions each where the flip-flop sfc is set and where sfc is reset. Thus, there are four terms or'ed together in the equation defining ssfc which is asserted to set flip-flop sfc and in the equation defining rsfc which is asserted to reset flip-flop sfc.

Refer to block 409, it was noted previously that the one (O) and zero (Z) lines may be exclusive-or'ed together to create a reconstructed clock which transitions with each bit of data that is received. This is true in the present case also, however, exactly one of the flip-flops sfa, sfb, or sfc changes state in response to a transition or change in state of either the O or the Z input. Thus, sfa, sfb, and sfc may be exclusive-or'ed together to create a reconstructed clock oclk as is done in block 409. There are short response delays between reception of a transition in the O or the Z inputs and the assertion of the corresponding change in sfa, sfb, or sfc. Thus, the timing of the changes in the sfa, sfb, and sfc flip-flops is closer to the timing in the assertion of the output data value making this expression a better one to use at least in some applications. It should be understood, that the exclusive-or of the O and Z inputs may optionally be used and that derived logic terms other than sfa, sfb, and sfc may also the configured such that they can be used to derive the clock signal.

Block 410 contains Verilog statements defining two flip-flops. The first has an output podo which is set to the 1/0 value of the odd bit immediately after the state of sequencer 400 responds to the receipt of an odd bit by transitioning to one of its odd states. The value of podo persists for one clock period of oclk at which time it is set to the value of the next odd bit. The second has an output evo which is set to the 1/0 value of the even bit immediately after the state of sequencer 400 responds to the receipt of an even bit by transitioning to one of its even states. The value of evo persists for one clock period of oclk at which time it is set to the value of the next even bit. podo is set when the sequencer 400 has advanced to states five or six and is reset when the sequencer 400 has advanced to states zero or three. evo is set when the sequencer has advanced to states one or two and is reset the when a sequencer has advanced to states four or seven. In addition to pairing or grouping the odd and the even response, podo and evo each persist for a full clock period whereas the states of sequencer 400 persist for only a half clock period. The transitions of podo extend approximately from a rising edge of oclk to its next rising edge and the transitions of evo extend approximately from a falling edge of oclk to the next falling edge. Depending on circuit timing, the point at which these signals are sampled may vary. In this design, the signals are sampled on the clock edge which is approximately at the midpoint of the stable period of the signal.

Block 411 references a Verilog module ffdc that defines a positive clock edge triggered type d flip-flop with clock input c, clear input clr, d input d, and q output q. The module ffdc_1 is the same as the module ffdc except that it is negative clock edge triggered. The first flip-flop odof samples podo at its midpoint and outputs the signal odo which is synchronized with oclk (In this block, oclk is used as the system clock) and which is delayed by one half clock period. The second flip-flop pevodf samples evo at its midpoint and outputs the signal pevod which is synchronized with oclk and which is delayed by one half clock period. The third flip-flop evodf samples pevod at its midpoint and outputs the signal evod which is synchronized with oclk and which is delayed by one half clock period from pevod evod is delayed by one clock period from evo so that odo and evod are synchronized with each other and transition on the negative of edge of oclk. evod and odo may be handled readily as an even/odd data bit pair in a synchronous circuit having oclk as the system clock.

The one zero transmission protocol a pair of binary signals and associated signaling lines and the transmitted signals in general do not come close to maintaining DC balance. Here DC balance refers to an average value of approximately 0.5 for assigned values of 0 and 1 for the zero and one transmitted states, respectively. It is desirable to have a code where the DC average is close to the average of the two values assigned to the binary transmission states and for which the average does not build too much in one direction before there is offsetting content in the opposing direction to return the long term average approximately to the mid point value. This property is necessary to be able to run the signal through a transformer without material change in the waveform. For transformer coupling, a differential signal is normally used so that a binary 1 is represented by a signal level of one polarity and a binary zero by a signal of approximately equal amplitude but of the reverse polarity. For the preferred coding technique to be detailed hereinafter, when the data dependent transitions are centered between the clock transition a one bit spends equal time in the one and zero state so a single one is balanced. For the zero transmissions, the coding is such that for each zero transmission, the entire transmission period is spent in the transmission state which is opposite that of the transmission state for the immediately preceding zero transmission. Thus, each pair of zero transmissions with no intervening zero transmission average to a DC balanced state. It is also desirable to be able to recover a periodic clock signal from the transmitted data stream and to have a way to use this as a data recovery and even as a system clock on the receiving end. This recovered clock may in some cases be used to clock a logic circuit to generated a return data stream. It is also desirable to be able to recover the data without the need for a clock frequency which significantly exceeds the bit rate of the data stream. It is also desirable to have relatively few data line transitions per bit transmitted. As noted earlier, the traditional clock data averages about 2.5 transitions per bit and requires a pair of signals, the one zero requires exactly one transition per bit and requires a pair of signals and the scheme to be described averages about 1.5 transitions per data bit and requires only one signal. The transmitted waveform for the bit encoding is like that used in a certain variant of a data transmission scheme which is referred to as Manchester encoding. The specific encoding scheme has certain advantages so that it has been chosen for the preferred embodiment but it should be recognized that many of the features of the invention remain valid with different encoding schemes.

As an option another transmission scheme such as separate clock and data or the one zero might be used in place of the preferred variant of the Manchester encoding which combines the clock and data into one signaling stream to transmit it from the interface to the remote unit.

As will be described in detail below, the encoding scheme includes one bit period intervals to represent or transmit each binary bit value and each of these intervals preferably begins with a mandatory binary bit value transition so that there is exactly one clock transition per bit in a sustained data stream. For successive bits, each bit period interval is started by the mandatory bit value transition at the start of the interval and ended by the mandatory bit transition at the beginning of the next bit period interval. Each of these intervals has zero or one intermediate binary bit value transitions which are chosen so that the transmitted value may be inferred from the pattern of the absence and the presence of these transmitted intermediate transitions. In a preferred arrangement, a binary 1 is represented by the presence of a single intermediate binary bit value transition in the interval which represents the bit and a binary zero is represented by the absence an intermediate bit value transition in the interval which represents the bit.

To encode the data, a delay line whose delay time is normally based on the length of the bit period interval may be used with associated logic to combine the intermediate data transitions with mandatory clock transitions which occur between each of the bit period intervals. Optionally, the transmitted stream may be generated, for example, by a synchronous logic circuit.

To decode the data, a feature of the preferred embodiment is to use a delay, preferably, a single delay, in a circuit which inhibits certain logic elements from responding directly to the intermediate clock transitions which encode the transmitted data and to enable these elements to directly respond to the clock transitions which occur between each of the bit period intervals. It is then desirable to determine the transmitted bit values based on comparison of levels which infer the relative direction of the clock transitions at the start and at the end of the interval whose bit value is to be inferred. The circuit is preferably arranged so that this level comparison which indicated the bit value persists for a substantial portion of the bit period. It is also a desirable result that a derived clock signal with one clock cycle per bit or optionally with one half clock cycle per bit may be derived from the logic signals including a signal or signals which pass through the delay element. The derived clock signal may also be used as the clock for logic to generate a return data stream and to encode the signal with the bit period interval boundary clock transitions and to further establish a reasonably controlled and desirable timing phase relation between the clock transitions at the bit interval boundaries and the intermediate transitions which represent the transmitted data value. In the chain of events which include receipt of a reference clocks signal and outputting of a phase related data signal, the frequency and phase reference effectively propogate from the clock reference through the remote device to the returned data signal.

Figure 5:
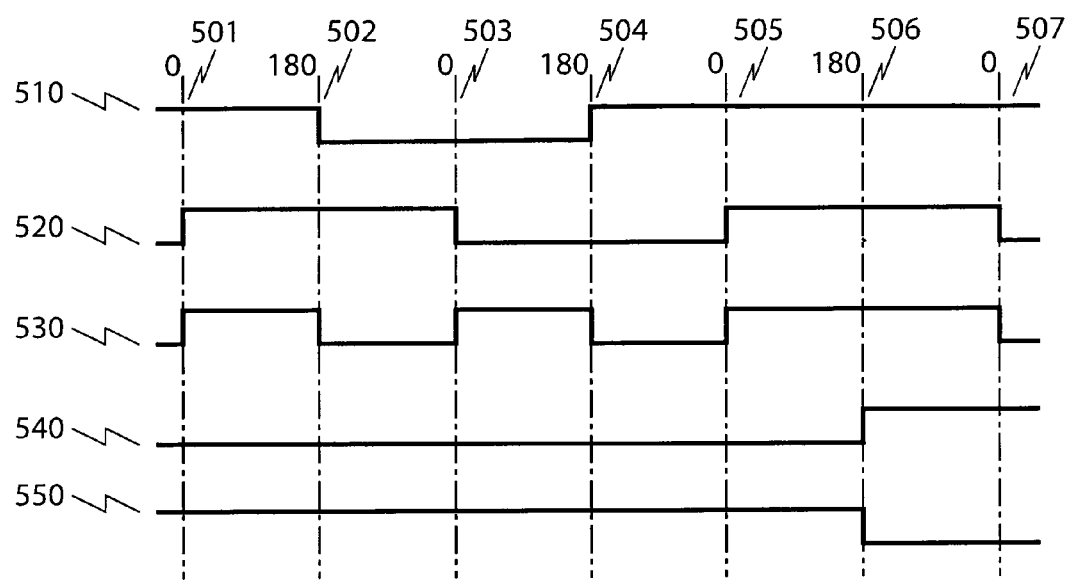
FIG. 5 depicts waveforms for a three bit long sequence.

Referring to FIG. 5, waveforms for a three bit sequence, binary 110, with the encoding for the first, second, and third bits extending from 501 to 503, 503 to 505, and 505 to 507, respectively. The vertical timing marks for the bit boundaries at 501, 503, 505, and 507 are assigned a phase of 0 degrees for reference and 360 degrees are assigned to each bit period for reference so that the mid bit positions are assigned a reference phase of 180 degrees as indicated for the vertical timing marks at 502, 504, and 506. Trace 510 has a single transition at 180 degrees for each of the one bits and no transition otherwise.

Signal 520 is a clock with transitions at the 0° point and trace 530 is formed by taking the exclusive nor of signals 510 and 520. This is the signal waveform of the type preferably transmitted from the interface to the remote unit to communicate the reference clocks and data. Trace 510 is like the one signal used in the one zero encoding. Trace 540 which is normally not used here but inferred by the absence of transition at the 180 degree phase point for bits of zero value would be the zero signal in a one zero signaling scheme. Trace 550 is the recovered data. It is only coincidental that this is the complement of trace 540.

There are prior art systems for which a master unit issues a command to a slave followed by a sequence of discrete clock pulses to which the slave responds by returning a sequence of discrete data bits. With such systems, there is normally a one-to-one correspondence between clock pulses issued and data bits returned and this correspondence is normally used directly to determine the placement and meaning of each of the data bits which are returned. Furthermore, the data rate is normally slow enough that provision to align the phase relation is unnecessary.

Figure 6:
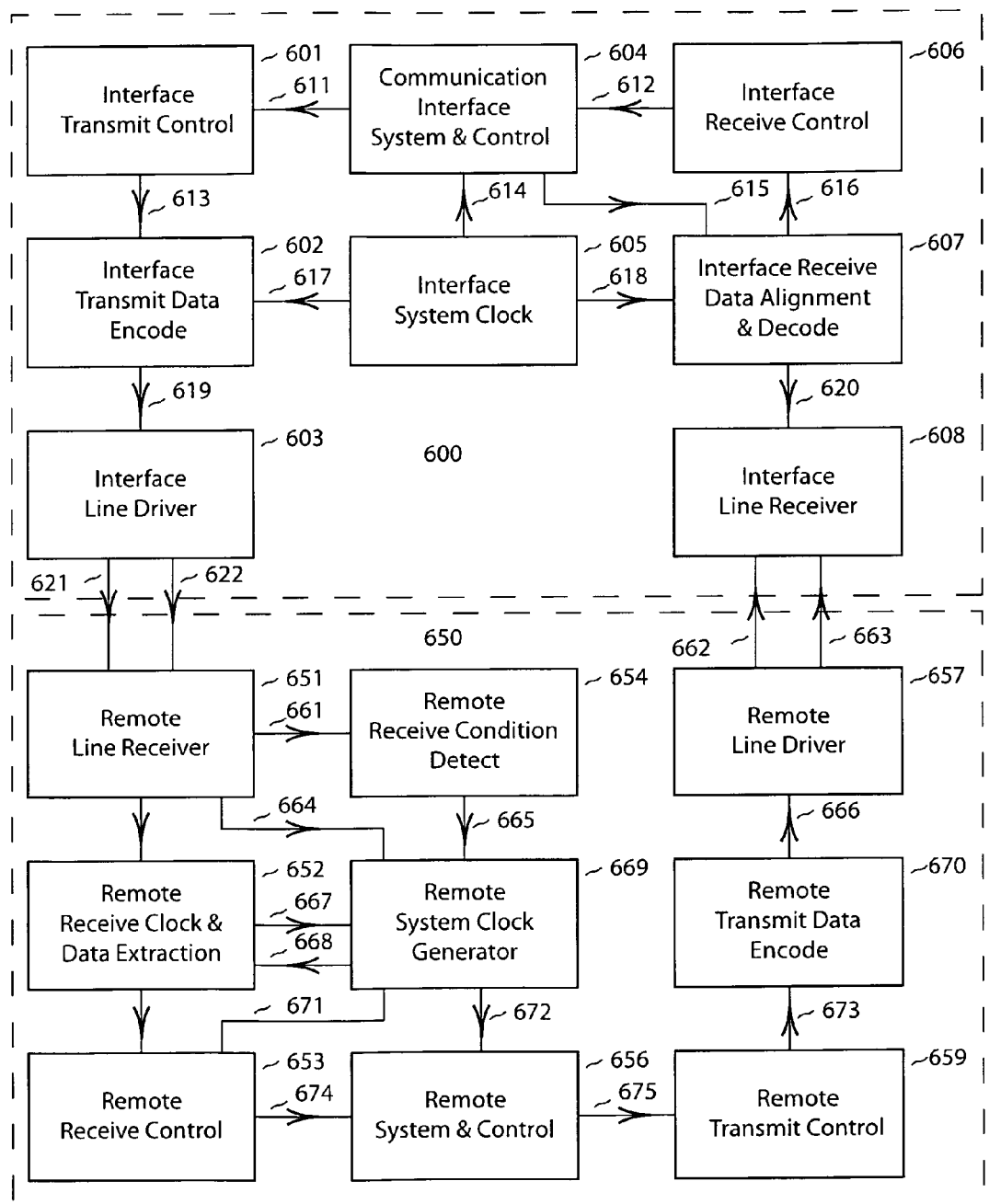
FIG. 6 depicts an interface unit in communication with a remote unit.

Refer to FIG. 6, an interface unit 600 communicates serially with a remote unit 650. It should be understood that the interface unit, the remote unit or both units may comprise a micro-controller. This remote unit may, for example, be a camera with a serial interface. The interface unit has a communication system control 604 and a system clock 605. This system clock is preferably used as the frequency reference for the remote unit 650 as will be described. The serial interface in the interface unit 600 includes a transmit section having blocks 601, 602, and 603. These blocks are used to transmit instructions and data to the remote unit 650 and also to transmit a reference clock whose use preferably includes the following three functions. First, the clock 605 is preferably used as the clock for the serially transmitted data. Second, the clock 605 is preferably used as the frequency reference for the oscillator or clock generator for remote unit 650. This is done by reconstruction and preferable multiplication of the reference clock which is extracted from the received clock and data signal. Frequency multiplication is preferably done using delay elements but may also be accomplished by other techniques including use of a phase locked loop. Third, the clock 605 is preferably used as the frequency reference for the data transmitted serially from remote unit 650 to the interface unit 600. Even if the data stream that is returned from remote unit 650 to interface unit 600 contains adequate timing information to be decoded without another reference clock, it is normally easier to accomplish the decoding process if the data returned over the differential pair 662 and 663 is timed so that it has a relatively stable frequency and phase relationship to the system clock 605. As will be described in detail, this is accomplished by encoding the data signal transmitted on differential lines 621 and 622 synchronously with the clock 605. This transmitted clock and data signal is used in remote unit 650 to construct and/or synchronize the clock signal 669. This clock signal is preferably used as the system clock for remote unit 650. In turn, the remote unit 650 encodes the data signal returned to the interface unit 600 over the differential pair of lines 662 and 663 synchronously with the system clock 669. Thus, through this chain of synchronized clock references and system clocks, stable frequency and relatively stable phase relations between the received data and the interface clock 605 can be maintained. Instead of requiring the extra signaling bandwidth to provide timing data in the signal returned on differential lines 662 and 663, it is only necessary to have enough information in the signal returned on differential lines 662 and 663 to establish that a satisfactory phase relation exists between the data received by interface unit 600 and the phase synchronous system clock 605 to decode the data. It is preferable to provide a unit to adjust the phase relation between the received data stream and the system clock 605 in order to bring the data into a satisfactory phase relation or alignment with the system clock for satisfactory decoding of the input data stream. It is also preferable to use the phase detector to determine when a satisfactory phase relation or alignment is established and to provide a unit to respond to the condition of the phase relation and to adjust the phase relation so that it is satisfactory to receive the incoming data. Phase locked loops based on a variable frequency oscillator may be used for this purpose but it is preferable to use adjustable or selectable delays and/or choice of clock edges to sample the data to adjust this phase relation. In alternate designs, phase alignment may be accomplished at nearly any point in the path over which the clock reference is maintained. For example, by an adjustable delay in transmission of the clock and data stream from the interface to the remote unit. Since the system is preferably designed so that the phase relation tends to be stable (i.e. relatively stable) over time, particularly in the short term, it may only be necessary to make this measurement and adjustment periodically. Possibilities include establishing the phase by design, adjusting the phase as part of the initial production calibration, adjusting the phase at startup, periodically adjusting the phase to compensate for changes in operating conditions such as changes in ambient temperature, or by providing continuous or nearly continuous feedback control to maintain proper phase relationship between the incoming data and the clock used to decode the data. As an option, clocks in the system which are not used to maintain the phase synchronization of the data do not have to be synchronized with the clocks described herein, but then data must normally be synchronized between these optional clocks and the data synchronized clocks and other clock references must be provided to independently reference and stabilize additional non-data transmission related clocks. In some designs, receive data differential line pair 662 and 663 are multiplexed and receive data from two or more remote units similar to 650. In some cases, differential line pair 662 and 663 may be time shared and in other cases additional pairs similar to 662 and 663 may be added. In either case, phase between the received data signal and the system clock signal in the interface unit may often be different from different remote units. In such cases, the system must adjust rapidly enough to satisfactorily respond to the phase differences. As an alternative option, satisfactory phase adjustment parameters may be established and recorded for each of the multiplexed units, and the communication interface control 604 may set the correct phase adjustment parameters for each of the designated remote units to receive data from the designated unit. If separate receive channels are used, another option is to provide individual phase alignment for each of these channels. When this is done, certain components such as the phase detector may be shared between channels when the requirement is such that 100% dedication to a particular channel is not required. The preferred embodiment utilizes differential pairs of wires for the transmission paths. It should be understood that most of the features of the invention apply equally well for systems which use an optical transmission path or which may also use a radio frequency transmission path or a single-ended transmission path which may, for example, be a single wire with the signal referenced to a common ground or a coaxial or other shielded cable.

The interface control unit 601 queues data to be sent and sends it to the interface transmit data unit 602. The data unit 602 preferably encodes the data signal as a variant of the Manchester code and sends it to the line driver 603. The line driver 603 which may optionally include transformer coupling transmits the data signal, preferably on differential lines, to the receiver of the remote unit 650. The system clock signal 618 is preferably used to generate the timing for the serially transmitted data. In order for this clock to be effective as a frequency reference for the receiver 650 and for the data stream returned on the differential pair of transmission lines 662 and 663, it is preferable to use a transmission protocol where transmission is normally continuous and where the transmitted clock information can be easily separated from the transmitted data. It is also anticipated that for many systems higher data rates must be received from the remote unit 650 module than need to be sent to the remote unit. Thus, with these systems, for data sent from the interface to the remote, the overhead of transmitting a clock bit along with each data bit is reasonable. The transmission protocol needs to include information to enable the remote unit 650 to frame the data and to separate transmitted data from the sustained transmission of timing information during an idling period in data transmission. A relatively simple protocol similar to the RS232 protocol for which information is transmitted eight bits at that time and for which a one "start" bit is inserted in front of each eight bit data byte may suffice. As a general option, particularly in systems where more data is sent to the remote from the interface than from the interface to the remote, the reference clock may be placed in the remote unit and the clock may be reconstructed in the interface unit so that the clocking functions in the remote and the interface may be generally interchanged from what has been described. Also, the naming of the devices as interface and as remote have been used for convenience in the examples and it should be understood that many features of the invention still apply to modules which do not serve as remote and/or interface units. Furthermore, in certain cases, the communication and clock recovery schemes may be applied to communicate clock and data signals between units which are in close proximity to each other.

The remote unit 650 has a system control unit 656 and a remote clock generator 669. The remote unit preferably includes a special condition detect unit 654 which monitors the remote unit receive channel. The communication interface unit 600 should preferably have facility to signal this special condition on the differential pair of transmission lines 621 and 622 and a remote unit 650 should preferably have the capability to detect this special condition even in startup mode when the system clock may not be running and when the receiver in unit 650 may not be calibrated to properly decode the received data. A simple and preferred way to satisfy these objectives is to stop or pause normal data and clock transmission on differential lines 621 and 622 to signal the special condition. Then the receive condition detect unit 654 may simply be a module which responds to the transmission paused condition on differential lines 621 and 622. Since, during normal operation, transmission is continuous in order to provide a continuous clock reference, the stopped or paused condition may be intentionally used at startup to initiate appropriate system reset and system clock initialization sequences. A differential line receiver 651 which may optionally have a transformer is used to convert the differentially transmitted data to a serial binary encoded data stream signal. The reference clock and the data are extracted in block 652. The data is queued and initial formatting such as organizing the data into bytes and stripping out the control and idling bits is accomplished in block 653. The data is passed to the remote system and control unit 656. The remote system may, for example, be a camera with a serial receive interface for receiving instructions and clocking information and a serial transmit interface for returning the relatively large volume of camera picture data to the interface unit 600.

In the remote module 650, the remote system and control unit 656 places data to be serially returned to the communication interface 600 in module 659. If module 650 is, for example, a camera unit, the syntax and organization of the returned data may be closely linked to the way the image data is generated. For example, with many cameras the image data is processed and converted from analog to digital form and serialized on a pixel by pixel basis. This is normally done synchronously with the system clock and normally conversion and transmission are done on a row by row basis with a clock synchronized and uninterrupted flow of data while successive pixels in the row are read. There are normally short pauses of adjustable duration between reading of rows and longer pauses between reading of successive frames. In applications for which the camera data is sent back to the communication interface in a relatively raw form, it is preferable to retain a low-level transmission protocol. This could include, for example, row by row headers to establish framing and perhaps to indicate the length of the row. The length of the row might be indicated by indicating the number of bytes in the transmission for the row in a field which might precede the transmission of the pixel data for the row. In some cases, the interface unit can determine the exact length and framing of the response from the command. However, in general it is preferred to establish framing of the data returned to the interface from the content of the data stream itself. With use of the system clock in the interface unit to recover the data, knowledge of the framing of the data and of whether a data bit is being received or not is very difficult to ascertain from a low-level look at the returned data stream without inserting a lot of extra bits to provide this information at a low level. It is preferable to frame larger packets of data rather than to substantially inflate the volume of data which is sent from the remote unit 650 to the interface unit 600 by inserting a large number of control bits at a low-level. Using the techniques of this invention, it is reasonable to generate a remote system clock in block 669 which has a duty cycle which is reasonably close to 50%. Thus, it is reasonable to use this clock to generate what may be referred to as a double bit rate data stream, that is, a data stream for which there is a new bit of data for each half cycle of the system clock. This requires digital logic capable of preferably glitch free generation of a bit stream which may have a transition at each edge of the system clock. For digital logic circuits, it is normally desirable to take or directly derive the output from flip-flops which are clocked by the system clock. Such flip-flops respond to only positive or optionally to only negative but not to both edges of the system clock limiting the flip-flop output to a maximum of one transition per full clock cycle when they are used in a normal clocked mode. As described in the section of the patent dealing with the one/zero transmission protocol, the one signal or the zero signal may be generated at a double data rate by use of a straightforward asynchronous logic circuit or by multiplexing two out of phase signals using an exclusive-or function. Thus, a preferable option for encoding for a bit rate higher than the clock frequency is to encode the return data by having a transition for each binary one to be transmitted and no transition for each binary zero to be transmitted. This is equivalent to the encoding for the one data line for the one/zero transmission protocol. The zero signal of the one/zero pair is preferably not sent but is inferred when there is a receive data clock bit period for which there is no transition on the receive transmission line, that is on the differential receive line pair 662 and 663. For this transmission encoding, a one is encoded as a bit period for which a transition is present and a zero is encoded as a bit period for which a transition is not present and to maximize the bandwidth utilization for the return transmission from the remote unit, clock transitions are not inserted at the bit boundaries as they are for the variant of Manchester encoding used for data sent to the remote unit. In the above, an option is to transmit the zero signal of the one/zero protocol and to infer the content of the one channel. In this case, the data line transitions will occur to signal the transmission of a zero rather than to signal the transmission of a one.

The transmission format just described is not DC balanced and is not good for transformer coupling. When transformer coupling is needed, a data encoding such as 8B/10B may be used to provide a DC balanced data stream for transmission. The 8B/10B transmission format is in prior art devices including used for gigabit Ethernet transmission and also in the high-speed serial ATA interface for data communication with disc drives. Using the format, 8 bit bytes are replaced by a 10 bit code and a technique to maintain DC balance is employed. This encoding in addition to providing DC balance, provides a reasonable number of data transitions per bit which are good to measure phase. Also, in addition to the 256 8 bit data values, several control codes including framing characters are included in the 10 bit coding scheme so that framing and signaling information may be interspersed with the data being transmitted. In some systems particularly when transformer coupling is not needed and when the bit rate is not higher than the clock frequency or when other techniques are used to generate the data stream, it may be preferable to use simple level encoding such as would be used for the data stream when serial data is sent on one signaling channel and a clock signal is sent on a second data channel. In any of the transmission methods alluded to above, particularly with the 8B/10B transmission scheme which guarantees frequent transitions on the data line, it may be possible to recover the clock by phase locking an oscillator to the transitions at the boundaries of the data bits. It is preferable, however, and normally requires less hardware to take advantage of the fact that in preferred configuration the data is already being returned to the interface unit 600 in stable phase relation to system clock 605. Thus, alignment of the phase of the incoming data stream to the system clock or vice versa utilizing a simplified phase detection and a combination of delays and/or active clock edge selections is preferable to implementation of a high-performance phase locked loop. To detect phase of the data received by the interface unit relative to the system clock of the interface unit, there must be some signal level transitions on the receive data line. If there are an adequate number of signal level transitions in normal received data, this data may be monitored to determine the phase relation. In some implementations, it may be advantageous to design the remote unit 650 so that it will send a special calibration sequence periodically or in response to a command from interface unit 1000. Such a sequence may be optimized to facilitate the phase detection and receive channel synchronization process.

Figure 7:
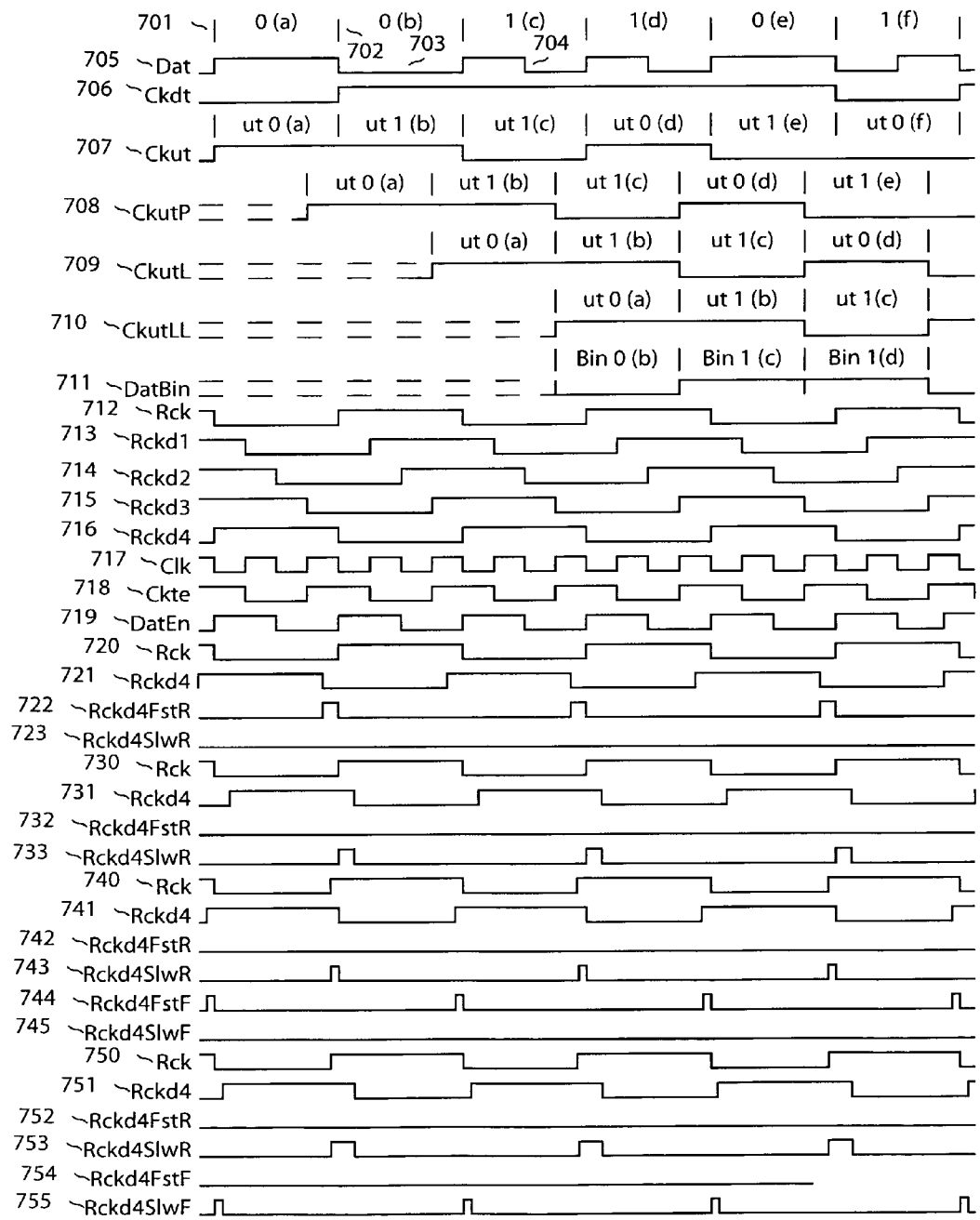
FIG. 7 depicts a data signal for transmitting clock and data information with waveform from related signal processing circuits.

Referring to FIG. 7, signal trace 705 depicts a data signal for transmitting clock and data information from the interface to the remote unit. The encoding preferably used is a variant of Manchester code. Vertical slashes 701 and 702 denote the boundaries of the first bit 0(*a*). The definition which is given here for the variant of the Manchester code which is used is not the conventional one but is one which is convenient for the clock extraction and decoding techniques which are used. Optionally, other encoding techniques including other variants of Manchester encoding may be used. Preferably, all bit periods are nominally equal in length and every bit shares a clock transition with each of its neighboring bits at each of its bit boundaries netting one guaranteed clock transition per bit. For the encoding scheme chosen, a bit with no additional data line signal transition between these boundary clock transitions is a zero and a bit with exactly one additional signal transition between these boundary clock transitions is a one. Since these additional intermediate data stream transitions are used to define a one bit as opposed to a zero bit, that is they encode the data stream information, they will be referred to as the data transitions whereas the periodic transitions which occur at every bit boundary will be referred to as the clock transitions. The Dat signal 705 represents the binary number 001101 for the successively transmitted bits (a), (b), (c), (d) (e), and (f). Recovery of the encoded clock and data from 705 is facilitated by using flip-flops in combination with a delay timing circuit, preferably a propagation delay, which serves to enable response of the flip-flops to the boundary clock transitions while inhibiting response of the flip-flops to the intermediate data transitions. In the implementation of the example, two flip-flops are used. The output of the first flip-flop is illustrated by trace 706. At 706 Ckdt is the output waveform 706 of a toggle flip-flop which is negative edge triggered having waveform 705 as its clock input and having an enable signal which is true at each of the bit clock boundaries but is false during the period when the data transitions occur for the one data bits. Trace 707 Ckut is similarly generated except that it responds to positive transitions of signal 705. Since there is a transition of one but not both of these signal's 706 and 707 at each of the data bit boundaries and there are no other transitions in the signals, the recovered clock signal 712 Rck is generated by simply taking the exclusive nor of signal's 705 and 706. An exclusive-or could be used resulting in an inverted waveform for the reference clock.

As an option another transmission scheme such as separate clock and data or the one zero might be used in place of the preferred variant of Manchester encoding which combines the clock and data into one signaling stream to transmit it from the interface to the remote unit.

A portion of the binary data stream which is recovered from signal 705 is shown in trace 711 in binary form with a low for a transmitted zero and a high for a transmitted one. This recovered data stream may be constructed in a pipeline delayed fashion as represented by the signal 711 by registering the value 707 in a three stage shift register whose successive bits are represented by traces 708, 709, and 710. The three bit shift register is shifted once for each bit period. The data stream output is generated as the exclusive nor of the first and third bits of the shift register. The signal 706 could be similarly used as the input to the three bit shift register in place of signal 707. The dashed portions of traces 708 to 711 represent values which are determined by one or more of the three bits which preceded bit (a) of trace 705. Since these values are not shown for trace 705, the values which would be derived from them are depicted by the dashed lines. The reason that the exclusive nor of the first and third bits of the shift register yields the reconstructed data stream is as follows. For each zero bit which is transmitted, there is no intervening data transition between the clock transitions at the bit boundaries. Thus, if the clock transition is positive at the beginning of the bit period for a given zero bit, there will be a negative clock transition at the end of the bit period and likewise if there is a negative clock transition at the beginning of the bit period there will be a positive clock transition at the end of the bit period. In either event, there is exactly one positive clock transition and one negative clock transition in the two clock transitions one occurring at each of the boundaries of the given bit period. This in turn means that the value of signal 707 will be toggled exactly once either at the beginning or at the end of the given bit period for a zero bit. Thus, for a given zero bit, the value of 707 for the bit period immediately preceding the given zero bit will mismatch the value of 707 for the bit period immediately following the given zero bit period. Thus, the exclusive nor of a signal representing the value of 707 in the bit period which immediately precedes the given zero bit period with a signal representing the value of 707 in the bit period which immediately follows the given zero bit period will be zero and this represents the value of the transmitted bit.

For a given bit period in which a one is transmitted, there is exactly one intermediate transition in the value of the data signal 705 and the signal 707 is inhibited from responding to the intermediate transmission but responds only to positive clock transitions at the boundaries of the given bit. Because of the intermediate data line transition for the one bit, the transitions at the boundaries of the given bit period for which a one is transmitted will either both be positive or they will both be negative. With reasoning analogous to that for the given zero bit there will be exactly two or exactly zero toggles in the value of signal 707 in response to the two data signal transitions of 705 at the boundaries of the given bit period in which the one is transmitted. An even number, which includes zero and two, of clocks of the toggle flip-flop brings it back to its original value. Thus, the exclusive nor of a signal representing the value of 707 in the bit period which immediately precedes the given bit period in which the one is transmitted with a signal representing the value of 707 in the bit period which immediately follows the given bit period in which the one is transmitted will be one and this represents the value of the transmitted bit.

The data trace 711 illustrates the exclusive nor of signals 708 and 710 and the recovered values for bits (b), (c), and (d) are shown. As indicated earlier signal 712 Rck is the exclusive nor of signals 706 Ckdt and 707 Ckut and is the recovered clock reference signal. Signal 713 was obtained by passing signal 712 through a one quarter bit period propagation delay. Signal 714 was obtained by passing signal 713 through a one quarter bit period propagation delay. Signal 715 was obtained by passing signal 714 through a one quarter bit period propagation delay. Signal 716 was obtained by passing signal 715 through a one quarter bit period delay. Signal 717 which is used as the system clock is formed by taking the exclusive nor of signals 712, 713, 714, and 715. This yields a signal which has four times the frequency of signal 712 and which is preferably used as the system clock and as the clock reference to generate the data stream which is returned to the interface unit. The delay may be constructed as a single delay element with taps. Other fractions of a bit period may be used. For example, five delay elements each adjusted to a delay of one fifth of a bit period may be used in place of the four delays with each adjusted to a delay of one fourth of a bit period and five out of phase clock signals may be exclusive-or'ed or exclusive nor'ed together to generate a clock that is five times the reference clock frequency. Signal 718 is the exclusive nor of signal 713 and signal 715 and is used as the enable signal for the toggle flip-flop circuits used to generate signal's 707 and 708. Signal 718 is one during the clock transition intervals and zero during the data transition intervals for the data signal 705. Signal 719 is the exclusive or of signals 712 and 714 and is used to enable sampling of the data signal 711 on the positive edges of clock 717. For each bit period of the data signal 711, signal 719 is one during a rising edge of clock 717 during an interval when the data signal 711 is stable.

When the delay is properly set, signal 716 Rckd4 should be nearly the same as signal 712 Rck but delayed by one bit period which causes square wave signals 712 and 716 to be 180° out of phase. A phase detection circuit and a feedback loop are preferably used to adjust the delay so that the total delay of the four cascaded delay elements is equal to one bit period. Furthermore, it is preferable to construct the delay elements using matched components on a silicon chip so that there is inherent matching in the periods of the propagation delays for each of the four delay elements and so that response to delay calibration adjustment may be substantially the same for each of the four delay elements allowing a common calibration control signal to be used. Also, it is preferable to make a phase comparison between signal 712 Rck and signal 716 Rck4 to make a determination of the error between the actual phase shift and the ideal 180° phase shift, to use this error to determine a correction signal, to pass this correction signal through a low pass filter, and finally to apply it, preferably equally, to the four propagation delay elements which are used to generate the signals 713, 714, 715, and 716. Since in the specific implementation, the signals Rck and Rckd4 are 180° out of phase, the up edge of Rckd4 should come at substantially the same time as the down edge of Rck and likewise the down edge of Rckd4 should come at substantially the same time as the up edge of Rck. For proper operation of the circuit in this example, the delay needs to be close to 180° and the duty cycle of the waveform needs to be close to 50%. It is preferred that a small deviation in the duty cycle from 50% should not adversely affect the 180° phase shift calibration setting. Because of a 180° phase shift used for the phase comparison for duty cycle's other than 50%, the shorter portion of the phase shifted signal will be compared against the longer portion of the reference signal and vice versa. To achieve a phase shift of substantially 180° even in this situation, it is helpful to use a phase comparison circuit that takes into account both the phase angle of the up edge of Rck relative to the down edge of Rckd4 and the phase angle of the down edge of Rck relative to the up edge of Rckd4 and to effectively average these two phase measurements in the process to arrive at the delay circuit correction value. An alternate option is to employ a phase shift of 360° for the signals to be compared possibly by extending the delay period to one full cycle of the reference clocks (two bit periods).

Traces 720 through 723 depict a phase comparison between the reference clock, Rck waveform 720, and the Rck signal after it is delayed by a nominal 180°. The delayed signal is shown as Rckd4 721. In this example, the duty cycle is nominally 50% and the phase or timing of the rising edge of Rck is compared with the phase or timing of the falling edge of Rckd4. The signal Rckd4FstR 722 is asserted when the falling edge of Rckd4 721 occurs while Rck 720 is low, thus coming before the rising edge of Rck 720. In the example, Rckd4FstR 722 is reset when Rck 720 is high. At least for the 50% duty cycle, the falling edge of Rckd4 721 should coincide with the rising edge of Rck 720 when the signals are 180° out of phase. When the falling edge of Rckd4 721 comes early as in this example, the delay is too short and needs to be lengthened. For this example, Rckd4SlwR 723 which is asserted when the falling edge of Rckd4 721 comes after the rising edge of Rck 720 remains zero. The control circuit, to be illustrated later, is configured so that the assertion of Rckd4FstR serves to lengthen the delay.

Traces 730 through 733 depict a phase comparison between the reference clock, Rck waveform 730, and the Rck signal after it is delayed by a nominal 180°. The delayed signal is shown as Rckd4 731. In this example, the duty cycle is nominally 50% and the phase or timing of the rising edge of Rck is compared with the phase or timing of the falling edge of Rckd4. The signal Rckd4SlwR 733 is asserted when the rising edge of Rck 730 occurs while Rckd4 731 is high, thus coming before the falling edge of Rckd4 731. In the example, Rckd4SlwR 733 is reset when Rckd4 731 is low. At least for the 50% duty cycle, the falling edge of Rckd4 731 should coincide with the rising edge of Rck 730 when the signals are 180° out of phase. When the falling edge of Rckd4 731 comes late as in this example, the delay is too long and needs to be shortened. For this example Rckd4FstR 732, which is asserted when the falling edge of Rckd4 721 comes before the rising edge of Rck 720 remains zero. The control circuit, to be illustrated later, is configured so that the assertion of Rckd4SlwR serves to shorten the delay.

In the first phase comparison example illustrated by traces 720 through 723, the phase delayed signal Rckd4 is not delayed long enough and a correction signal Rckd4FstR is asserted where the Fst portion of the suffix indicates that the delay is too short, fast, and the R portion of the suffix indicates that the phase comparison is made relative to the rising edge of Rck. The second phase comparison example illustrated by traces 730 through 733 is like the first except that the phase delayed signal Rckd4 in this example is delayed too long and Rckd4SlwR is asserted where the Slw portion of the suffix indicates that the delay is too long, slow, and the R portion of the suffix indicates that the phase comparison is made relative to the rising edge of Rck.

In the design, the duty cycle needs to be fairly close to 50% for the frequency multiplying circuit to function correctly. There is a range of duty cycles, however, for which the circuit will function properly and it is never expected that the duty cycle will be exactly 50%. The tolerance in a duty cycle for which the circuit will continue to function properly may be increased if the phase delay comparison is not adversely affected by a small error in the duty cycle of Rck. Traces 740 through 745 are an example where the high portion of the Rck waveform 740 is longer than the low portion. The delayed trace Rckd4 741 is depicted as it would appear with a nominally correct 180° phase shift. Here, since the shorter low portion of 740 is nominally aligned with the longer high portion of 741, the falling edge of 741 comes after the rising edge of 740 but the rising edge of 741 comes before the falling edge of 740. Curves 742 and 743 represent the result of a phase comparison between the rising edge of the wave form 740 and the falling edge of waveform 741 which is obtained in the same way as traces 732 and 733 in the example illustrated by curves 730 through 733. For the curves 744 and 745, the phase relation between the falling edge of 740 and the rising edge of 741 is indicated and the falling edge of 740 is the reference for these waveforms as indicated by the F suffix. The method of obtaining this curve is substantially the same as the method used to obtain the curves 742 and 743 in the example illustrated by curves 740 through 743. The change being that in each case rising is replaced by falling and falling is replaced by rising. Also, high is replaced by low and low is replaced by high when not referring to the signals containing the Fst or Slw suffixes. In the control circuit, the signals with the Fst suffix should both serve to lengthen the delay whether they were computed relative to the rising, R suffix, or falling, F suffix, edge of Rck. Likewise, the signals with the Slw suffix should both serve to shorten the delay whether they were computed relative to the rising, R suffix, or falling, F suffix, edge of Rck. In the example, with the nominally correct delay as illustrated, the delay shortening effect of Rckd4SlwR should substantially offset the delay lengthening effect of Rckd4FstF resulting in the capability of the circuit to maintain a phase delay that is substantially equal to 180° even when the duty cycle deviates from 50%.

The example illustrated by curves 750 through 755 uses the same combined rising edge and falling edge phase comparisons as the example illustrated by curves 740 through 745. The difference is that the phase shift of 751 relative to 750 is greater than 180° and Rckd4SlwR and Rckd4SlwF are each asserted.

Figure 8:
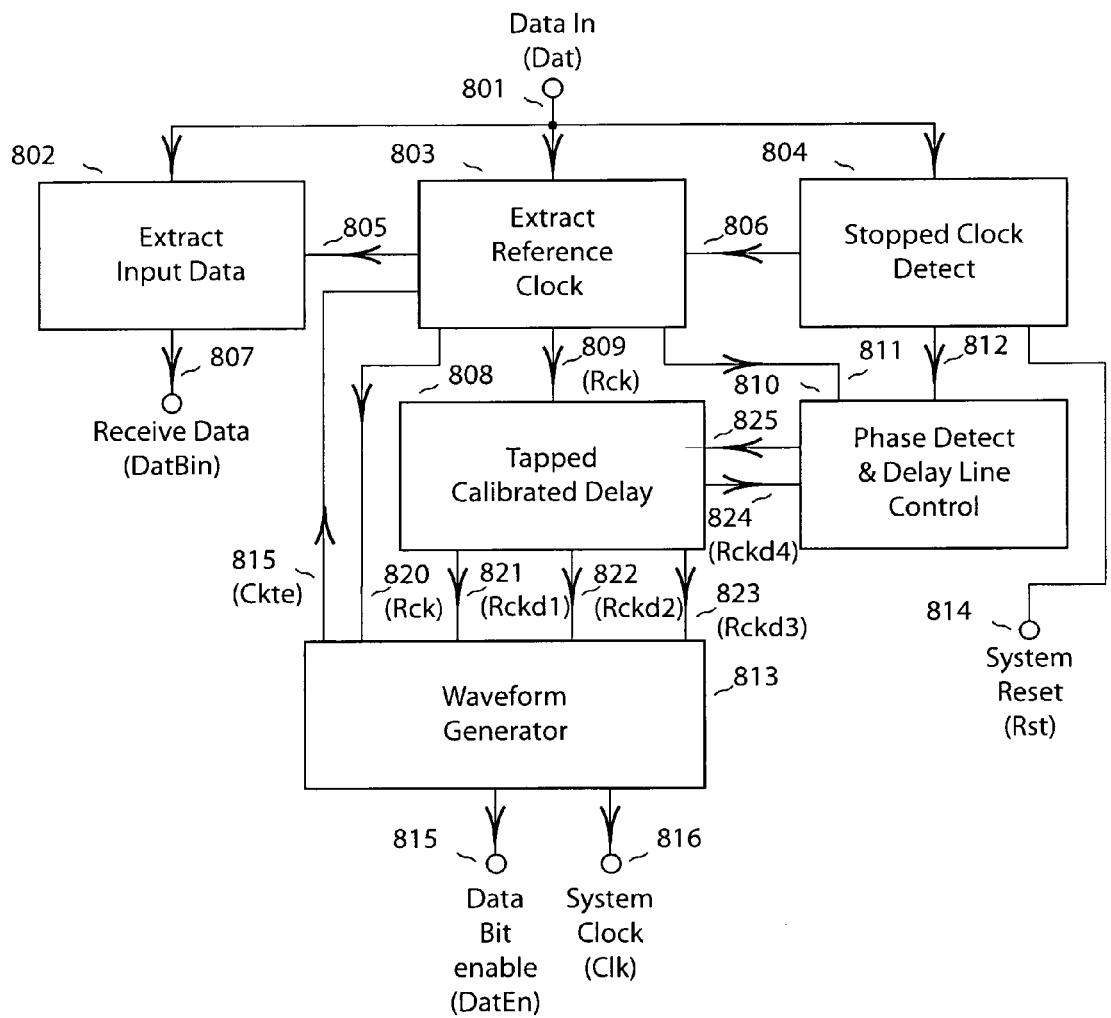
FIG. 8 depicts a block diagram that outlines input data processing for a remote unit.
Figure 9:
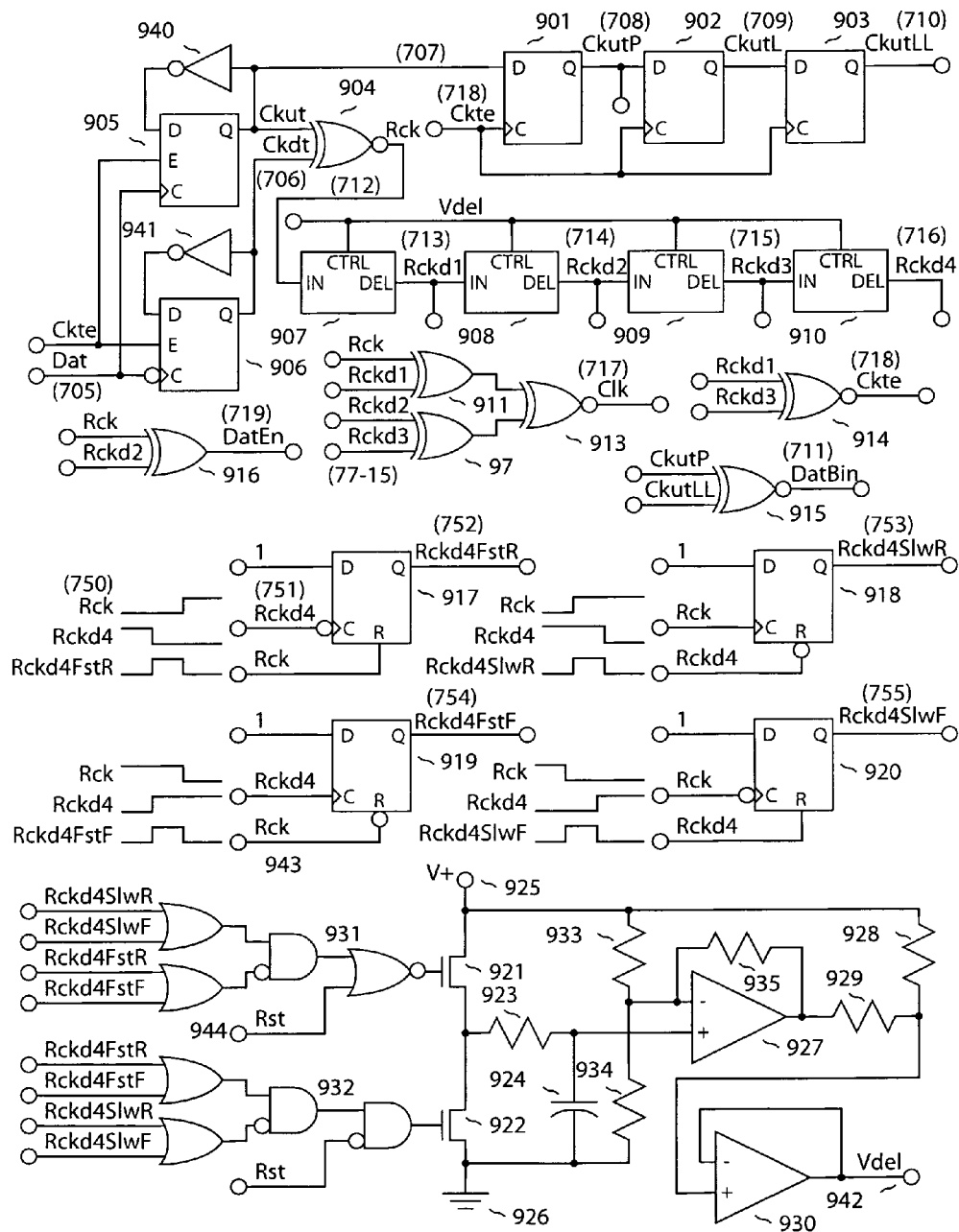
FIG. 9 depicts a simplified circuit diagram for processing the clock and data signal input and generating data and system clock outputs.

Referring to FIG. 8, is a block diagram that outlines input data processing for the remote receive function is depicted. This is one part of the function of the remote unit 650 of FIG. 6 and of the remote unit 1150 of FIG. 11. It generally parallels the detailed description presented for the signal traces of FIG. 7 and the circuit diagram of FIG. 9. Related signal names from FIGS. 7 and 9 are shown in parentheses in FIG. 8. Data is input at 801 and three features of this data are extracted by blocks 802, 803, and 804. In block 803, the reference clock is extracted and may be used as a reference for other portions of the circuit. In block 802 input data is extracted. In block 804, a pause in the receive data and clock transmission is detected. This pause in transmission is preferably used to initiate a startup sequence. For example, if there is a wide range in the delay element adjustment, it may be preferable to start with a particular delay setting, for example, with adjustment to the shortest delay, to another default delay setting, or to a previously used delay. Reset or other initialization of various functions may also be initiated by the paused received data and clock condition. Conditions of transmission other than a pause in the clock transmission may be used, however, the pause condition may need to be detected even when the delay of block 808 is seriously miss-adjusted. This miss-adjustment may in turn make it impossible to correctly decode the input data so it is preferable to use a special condition such as the pause in transmission which may be detected without the necessity to correctly decode the input data. Block 808 is a delay circuit which is preferably used to extract input data and also to generate various timing signals and optionally to logically combine the reference and delayed reference signals to multiply the reference clock to generate a higher frequency system clock. This delay is preferable to a phase locked loop when there is significant jitter in the reference clock frequency. Such jitter may be present when the clock used to generate the data stream containing the reference clock signal was generated by a phase locked loop circuit as is often used to generate a higher internal frequency in an integrated circuit which is referenced to a lower frequency external reference clock source. Or it may be intentionally introduced frequency dither to lower peak RFI emission. As is detailed in FIGS. 7 and 9, block 808 utilizes the delay circuit to generate a signal which may be compared to the reference clock to generate a control signal to properly calibrated the delay. The circuit which performs the phase comparison and generates the delay control signal is represented by block 810. The waveform generator clock 813 preferably generates a system clock which is a multiple of the frequency of the extracted reference clock and also generates various timing signals for use in the rest of the circuit.

With reference to FIG. 9, a simplified circuit diagram depicts logic elements and circuits which may generally be used to perform the circuit operations to generate the waveforms depicted in FIG. 7. The reference numbers for the related waveforms of FIG. 7 are shown in parentheses. Positive edge clocked D flip-flop 905 is clocked by the input data signal 705 and enabled by signal 718. Inverter 940 feeds the inverted output signal of flip-flop 905 back to its D input causing the output to toggle with each enabled positive transition of the input data signal which clocks the flip-flop. The signal 718 enables the flip-flop only during the clock transitions at the bit boundaries of the data input signal as described in the description for FIG. 7. Negative edge triggered flip-flop 906 and associated inverter 941 perform a similar function except that output signal 706 is toggled on the enabled negative edge transitions of the data signal 705. Exclusive nor gate 904 has as its inputs the signal 707 which toggles on the positive clock transitions of the input data signal and signal 706 which toggles on the negative clock transitions of the input data signal. The output signal 712 toggles exactly once for each of the clock transitions which occur in the input data signal. These clock transitions, by design, occur between each bit period yielding an approximate square wave with one transition for each data bit in the input signal making the frequency one half of the data rate of the incoming clock data signal.

The reference clock signal 712 is fed into the first stage of a four stage delay line having, preferably matched, delay elements 907 through 910. A preferred implementation of the adjustable delay is to use cascaded CMOS inverter logic elements for each of the delay of blocks; preferably using an even number of inverter elements in each block so that the output of each block is non-inverting. Each inverter adds an increment of delay and the number of inverter elements in each block should be chosen so that the combined delay of the cascaded inverter elements is in a range that may be adjusted for proper system operation. Each of the four delay blocks are supplied by the controlling voltage 942. It is a general property of typical CMOS inverter elements that their switching speed increases with increasing supply voltage. Thus, in a preferred design inverter elements whose switching speed increases with increasing voltage are employed. The voltage 942 is increased to decrease the delay of the delay line elements and decreased to increase the delay of the delay line elements. The inputs and outputs of the delay line elements are buffered or otherwise conditioned to interface properly with the rest of the circuit over the operational range of the delay controlling supply voltage 942. It is intended that, for proper operation, the delay of each of the four elements should approximately equal one quarter of a bit period. Thus the delay at the fourth tap 716 should be one bit period which is equal to one half cycle of the reference clock 712. The delay of one half cycle makes it convenient to use a phase comparison between the input reference clock signal 712 and the delayed clock signal 716 to determine the delay error and to generate the correcting signal 942.

Logic elements 911, 912, and 913 generate the exclusive nor of the reference clock 712, the clock delayed by one quarter bit period 713, the clock delayed by one half bit period 714, and the clock delayed by three quarters of the bit period 715. This logic function generates the system clock 717 which is four times the frequency of the reference clock 712. The logic element 914 generates the exclusive nor of the clock delayed by one quarter bit period 713, and the clock delayed by three quarters of the bit period 715. This generates the clock transition enable signal 718 which, with proper calibration of the delay elements, is true at the clock transition boundaries of the incoming data signal so that it serves to enabled the toggle flip-flop's 905 and 906 so that they respond only to the clock transitions of the incoming data signal 705. Signal 718 has one positive transition per bit period and is used to clock the shift register flip-flop's 901, 902, and 903. These flip-flop's shift in the signal 707 and signal 708 is the output of the first stage 901 of the three stage shift register and signal 710 is the output of the third stage 903 of the three stage shift register. The exclusive nor comparison by logic element 915 of the output of the first stage 708 and the output of the third stage 710 generates the data value 711 of the input data stream 705. The output 719 of exclusive-or gate 916 generates an enables signal to read the data output signal 711. Reference clock 712 and the reference clock delayed by one half bit period 714 are the inputs to the exclusive-or function 916.

Flip-flops 752 to 920 generate the four signals each representing a different component of the phase compare process. The general function of the four flip-flop circuit which performs the phase compare function is described in the description of the related signals for FIG. 8. In some detail for flip-flop 917, when the falling edge of the delayed reference clock signal 751 occurs while the reference clock 712 is low, the output phase indication signal 752 is set high in response to the falling edge of delayed clock signal 751 and remains high until it is reset when reference clock 712 goes high. Thus, the phase indicating signal 752 goes high when the falling edge of delayed clock 851 occurs while the reference clock 712 is low and it remains high until the reference clock 712 transitions to its high state. In other words it is high during the time interval between the falling edge of the delayed reference clock and the rising edge of the reference clock. Operation of the remaining three phase comparison flip-flop circuits is similar and will not be described in detail. Outputs 752 and 754 each indicate a condition when a transition of the delayed signals occurs before it is expected so that the action of assertion of either of these signals in the delay control circuit tends to increase the delay. Similarly, outputs 753 and 755 each indicate a condition when the transition of the delayed clock signal occurs after it is expected so that the action of assertion of either of these signals and the delay control circuit tends to decrease the delay.

The circuit 943 processes the four delay indicating signals 752 through 755 and generates an output signal 942 which varies over a desired target range and is generally increased by longer assertion of signals 753 or 755 which generally indicate that the delay is too long (slow) and is generally decreased by the longer assertion of signals 752 or 754 which generally indicate that the delay is too short (fast). To prevent a shorting condition in the particular circuit used, the delay is generally unchanged during periods when signals indicating both fast and slow response occur simultaneously. Prolonged assertion of a reset signal 944 causes the output delay control voltage to assume a high value to cause the delays to assume a short value. This is advantageous since, if the delay is approximately twice as long as it should be, false phase compare outputs may be generated. By initializing to the shortest delay, proper control can be established without assuming the long delays where these problems may be encountered. The reset signal 944 may be initiated by a pause in the transmission of the clock data signal 705 as discussed elsewhere. The output of logic block 931 goes low when either of the slow delay indicating signals 753 or 755 are asserted and neither of the fast indicating signals 752 or 754 are asserted or when the reset signal 944 is asserted. A low output from logic block 931 turns on transistor 921 pulling the input of resistor 923 to the positive supply voltage 925. This charges capacitor 924 through resistor 923 resulting in a filtering time constant and increasing the output voltage at 942. The output of logic block 932 goes high when either of the fast delay indicating signals 752 or 754 are asserted and neither of the slow indicating signals 753 or 755 or the reset signal 944 are asserted. A high output from logic block 932 turns on transistor 922 pulling the input of resistor 923 to ground 926. This discharges capacitor 924 through the filtering time constant decreasing the output voltage at 942. When Rst is not asserted and none of the fast or slow indicating signals 752 through 755 are asserted, neither of the transistors 721 or 722 is turned on so the charge on capacitor 924 will remain relatively unchanged resulting in a relatively unchanged voltage at output 942.

Resistor 923 and capacitor 924 serve as a low pass filter for the circuit. Resisters 928, 929, 935, 933 and 934 along with operational amplifier 927 and buffer amplifier 930 control the input range over which the voltage on capacitor 924 causes a change in the output voltage 942. The resisters also establish the range of the output voltage at output 942. Thus, this network of resisters and operational amplifiers controls the gain, the level shifting, and the output range of the controlling signal relative to the voltage on the low pass filter capacitor. As indicated earlier, the voltage 942 is used to control the delay of the four delay elements 907 to 910. In the preferred circuit, it serves as the supply voltage to cascaded inverter elements which are used to create the delays. In this arrangement, increasing supply voltage 942 increases the switching speed of the cascaded inverters which are used for the application decreasing the delay and, similarly, decreasing supply voltage 942 increases the delay.

With use of the delay line correction techniques, several points of general interest should be noted. In general, adjustable delays in the circuit span the range from a fraction of a bit period to several bit periods and correct operation may often be maintained with errors of a significant fraction of a bit period in the adjustable delay intervals. Thus, for many such systems, either the delay of delay elements in the circuit or the clock rate of the reference clock or data stream may often deviate by a number of percentage points from the nominally correct setting before errors occur in the data transmission or other performance characteristics of the circuit. Also, once a correct delay setting is established it is not normally necessary to change the delay setting until there has been an appreciable change in the circuit operating conditions such as, for example, initial calibration on power up if the delay setting values are not saved and restored, changes in propagation delay due to significant temperature changes or operating voltage changes in the circuit, or significant changes in the master reference clock frequency. Thus, unlike a phase locked loop oscillator which accumulates error on every cycle requiring constant and precise frequency correction, the circuits using the delay elements as described for data and reference clock extraction, for frequency multiplication, and for phase correction do not accumulate errors with every cycle and are generally tolerant to rather large changes in circuit operating conditions before a correction in the calibration is required. With tolerance to delay errors often in the range of several percent and with relatively slow change of environmental factors such as temperature which affect the delay characteristics, it is normally necessary to adjust delay settings at relatively infrequent intervals. With prior art systems which employ a phase locked loop, the error is accumulated with every cycle and, for data decoding, not only must the frequency be matched but phase must be held within a fraction of a bit period. Thus, frequency control of the controlled oscillator must the extremely stable and precise and small changes such as caused by significant jitter in a frequency such as the bit rate of the data stream to which the phase locked loop is locked may cause the controlled oscillator to lose synchronization thus resulting in data decoding and bit stream synchronization errors. With preferred implementation's using the delay elements, significant variation in the reference clock frequency is tolerated without requiring the delay adjustments to track these variations. Thus, because of the tolerance of the design to variation in the reference oscillator frequency; the reference oscillator frequency may be dithered over a restricted but significant frequency range using spread spectrum techniques to significantly reduce radiated interference while not adversely affecting performance of the circuit. A further advantage is that spread spectrum dither in the preferably single master frequency reference is generally replicated in the data streams and also in clock frequencies derived from the master frequency reference so that the benefits of the spread spectrum source may propagate through the system without having to provide multiple spread spectrum frequency generators.

The integrated circuit system MK5812 is an example of a clock generator which may be used for a spread spectrum interface system clock. Amplitude of the peak emission depends on many factors, including the spread used but for example reduction of 8 db to 16 db are claimed for the $3^{rd}$ through the $19^{th}$ odd harmonics by using the MK5812 part. In automotive application, the circuits are often placed close to receiving antennas. The MK5812 uses a saw tooth waveform for the frequency modulation. The frequency of this modulation should not be in the audible hearing or FM stereo encoding range or it is likely to be picked up as an audible tone or an FM receiver. The part utilizes, the smooth saw tooth modulation scheme to make it possible to track it with phase locked loops.

When delay elements rather than variable frequency oscillator with phase locked loops are employed as illustrated in the preferred embodiment, the design should be tolerant to random or pseudo random dithering so that more chaotic dithering techniques as are often used for switching power supplies may be used.

Figure 11:
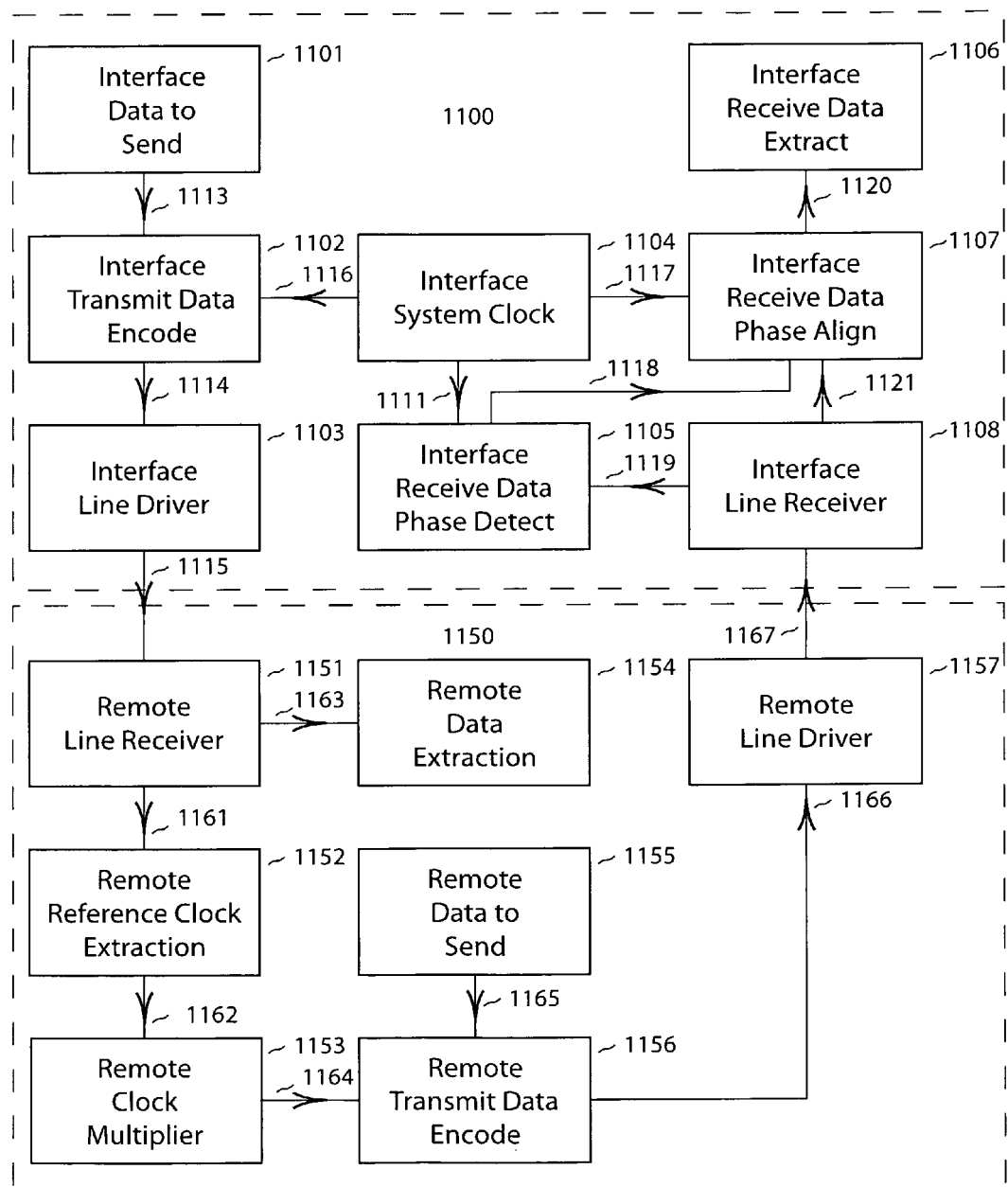
FIG. 11 depicts a block diagram of a system that emphasizes the clock and data relationships in an associated system.

Systems built in accordance with the block diagrams of FIG. 6 or FIG. 11 may be constructed such that the data stream from the remote unit is synchronized with a local clock in the interface unit. A preferred application of the communication circuit is to send commands from an interface to a remote imaging device and receive returned imaging data from the remote imaging device. In such systems, the data being received by the interface from the remote imaging device would normally be high data rate imaging data. In such systems, which are built according to the specification for a preferred design, synchronization is maintained in a chain from the system clock in the interface device, to the data stream transmitted to and received by the remote imaging device, from this data stream received by the remote imaging device to a reference clock in the imaging device, from this reference clock to a preferably higher frequency remote imaging device system clock, and from the system clock in the remote imaging device to the data stream returned to the interface device. With transmission paths which may be of appreciable length and the relatively large number of interface steps combined with the high data rate, the phase of the returned data relative to the interface clock which was used as a frequency reference at the beginning of this cascaded timing sequence will normally vary substantially from unit to unit and perhaps additionally with changing operating conditions such as changing operating temperature and operating supply voltages. The general function of the circuit of FIG. 9 is to receive the data stream from the remote unit which is synchronous with the system clock because of the timing chain just described, to compare the phase of this returned data with the phase synchronized local clock, and to establish a phase relationship which is suitable to clock in the data or otherwise decode the received data stream.

Figure 10:
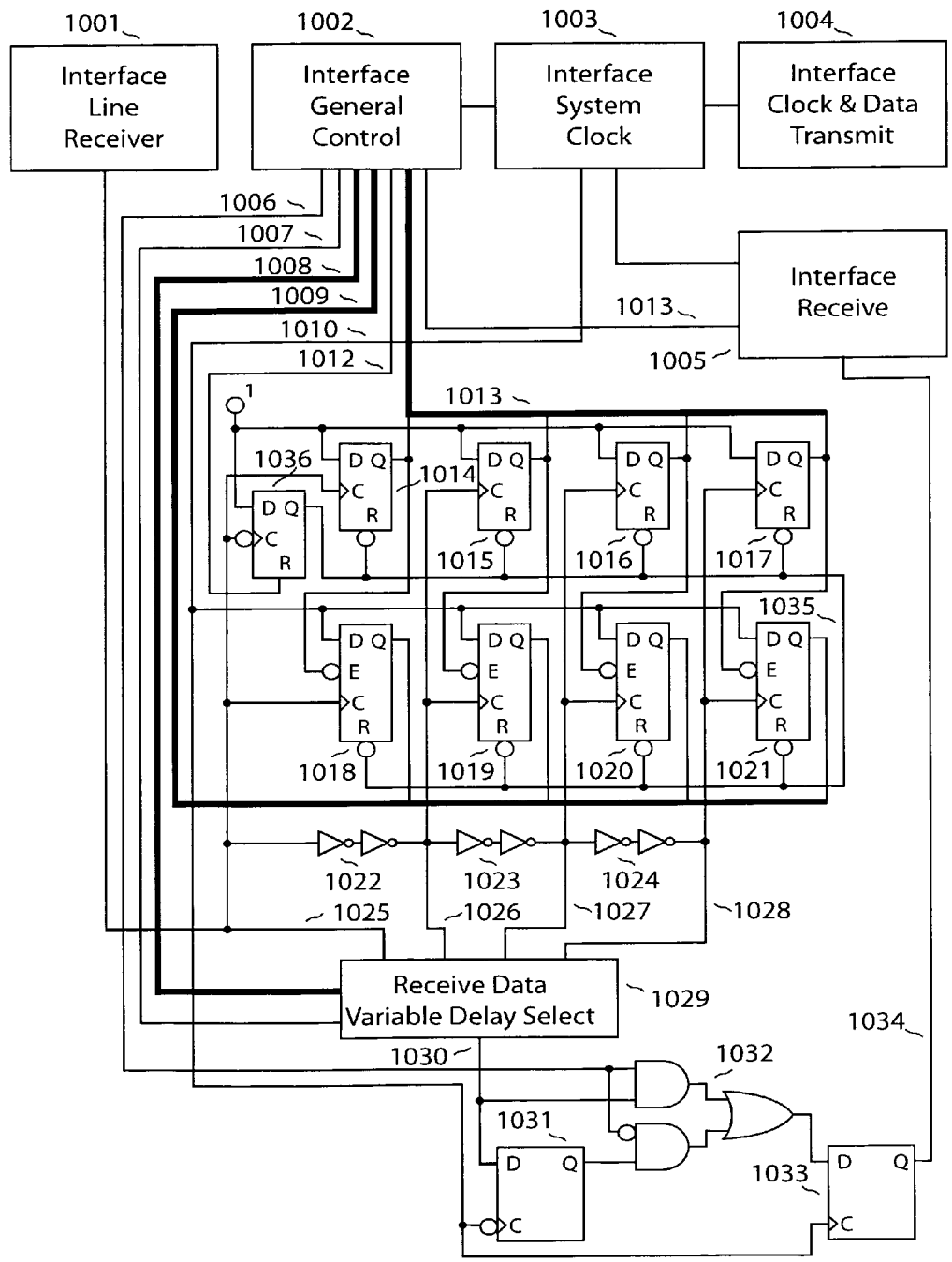
FIG. 10 depicts an interface unit circuit to receive data from a remote unit.

Circuits in accordance with that depicted in FIG. 10, data is received by interface line receiver 1001. The data passes into a tapped delay line represented by inverter pairs 1022, 1023, and 1024. In practice more inverters or alternative delay circuits may be used for these elements. The taps are at the undelayed input signal at 1025 after the first delay element at 1026 after the second cascaded delay element at 1027 and after the third cascaded delay element at 1028. A delay line with four taps and three delay elements is chosen by way of example and other numbers of elements may be employed, for example, 8 or 16 taps may be appropriate. Since it is normally satisfactory to make delay corrections at relatively infrequent intervals, it is appropriate to use a micro controller for the interface general control 1002. The delays of the tapped delay line segments are preferably approximately equal and the total delay is preferably somewhat greater than half of a bit period so that, in the system to be described, both levels of the clock will be included in a sample so that the timing and the rising or falling direction of the system clock edge relative to the data stream output at each of the delay line taps may be observed by reading the results from the clock sampling flip-flops as will be described. The interface system clock block 1003 is used to generate and synchronize the outgoing data stream with its embedded reference clock information in block 1004 and through the reference clock chain the relatively stable phase relationship to the system clock is retained in the data received by the interface line receiver 1001. However, due to variable propagation delays, the phase relationship between the received data and the interface system clock 1003 is preferably measured and adjustments are made to establish a phase relationship between the received data and the system clock which will allow proper decoding of the received data. In many systems, to reduce peak amplitudes of radiated interference, it is preferable to provide a system clock 1003 for which the clock frequency is varied or dithered over a restricted range in order to substantially reduce the peak amplitude of radiated interference.

There are a number of ways to measure this phase relationship including use of phase locked loop techniques. With certain restrictions on the format of the incoming data stream, it is even possible to recover the data stream clock entirely by observing the timing of the transitions in the incoming data stream and synchronizing a variable frequency oscillator with them using phase locked loop techniques. It is, however, generally advantageous to take advantage of the relatively stable phase relationship between the local system clock and the received data to simplify the decoding process and to make it tolerant to the use of such devices as spread spectrum dither in the frequency of the system clock.

In the preferred design, the system puts the incoming data stream through a tapped delay line. A mechanism is provided to record a snapshot of the state of the system clock for each of the delay line taps at the instant that a particular edge transition in the data stream occurs at the corresponding data tap. This snapshot is analyzed to determine how the incoming data is aligned with transitions of the system clock and the results of this analysis are used to determine a timing configuration which is suitable to receive the incoming data. In the preferred design, the active edge (rising or falling) of the system clock on which the data is registered is selected for best timing relative to the phase of the incoming data. In some designs which have relatively forgiving timing requirements, this selection may be adequate to properly receive the data. In the preferred design, in addition to selection of the system clock edge for which data is sampled, the delay line tap which provides satisfactory, preferably optimized, input data decoding performance is selected as the source for the input data in order to further improve the phase relationship between the system clock and the incoming data. There are a number of alternative options, for example, if a somewhat larger range of delay line adjustment is provided, the selection of the system clock edge to register the data may be omitted or if the system clock frequency is a higher, preferably integral multiple of the received bit rate, a divider may be configured to select the best clock edge on which to sample the incoming data. When a spread spectrum clock is used, it may be preferable to provide a technique to improve adjustment of the data and clock synchronization to properly handle the full range of frequencies of the dithered, spread spectrum clock. For example, multiple samples or readings of the phase relationship between the system clock and the input data may be taken and analyzed to determine a phase relationship adjustment which will work over the statistically sampled range of frequencies of the spread spectrum clock. Another option is to momentarily stop the spread spectrum dithering while making the measurement and then to make the phase correction adjustment to account for the actual frequency of the system clock when the phase measurement was made versus the range of clock frequency during spread spectrum operation. Other options include continuing spread spectrum operation but providing a means to monitor the spread spectrum frequency setting at the time at which the measurement is made and then accounting for this frequency relative to the frequencies over the total adjustment range when making the phase relationship adjustment. For example, a time varying signal is often used as an input to control the frequency variation in the spread clock, the value of this signal may be measured or used more directly in the analysis to determine a proper setting for the phase correction. In many cases, the range of frequency in the spread spectrum dithering may be small enough to be neglected in the phase measurement and adjustment process. In other cases, as alluded to above, the means used to control the spread spectrum frequency may also be used to make a parallel compensating adjustment in the phase relationship between the received data and the system clock or may be used to simply indicate the spread spectrum frequency setting at the time at the phase relation measurement is taken. In other cases the rate at which the system clock frequency is dithered may be slow enough for the data to system clock phase relationship adjustment to track frequency changes of the dithered system clock.

In the example circuit of FIG. 10, the phase relationship between the received data and the system clock are measured for rising edge transitions of the received data, falling edge transitions of the received data may propagate at a slightly different rate to the system clock, so in some systems it may be preferable to additionally monitor the phase relationship at the falling edge transitions of the data. Then the measured results of the phase relationship between the incoming data and the system clock taken for rising and for falling edge transitions of the received data may be averaged or otherwise reconciled to determine the phase correction adjustment to use. Implementation of this option is not shown in FIG. 10 but may be implemented using additional circuitry, for example, by adding counterparts of synchronizing flip-flop 1036 and of the sampling disable register and of the system clock sampling register all provided with additional control and readout logic and generally differing from the synchronizing, sampling and sampling disable flip-flops shown in that the synchronizing flip-flop for the negative edge sampling should be rising edge triggered and the flip-flops for the sampling and sampling disable registers should be negative edge triggered. The clock sources may be from the same delay taps 1025, 1026, 1027, and 1028. When phase is measured relative to a single edge direction for the incoming data, the falling edge may be used instead of the rising edge as was used in the example. An option in some implementations is to have a controlled inversion of the input data signal or other method to share common circuit elements to determine the phase relationship selectively for either falling or for rising edge transitions in the incoming data stream.

In more detail, the registers consisting of a sampling disable register with flip-flops 1014 through 1017 and a system clock sampling register with flip-flops 1018 through 1021 are used to sample the level of the system clock for each of the delay line taps 1025 through 1028 when a rising edge of the data stream appears at each of the respective delay line taps. The general control 1002 asserts a reset signal on line 1012 to reset synchronizing flip-flop 1036 causing its output 1035 to go low. The resulting low output of synchronizing flip-flop 1036 resets both the sampling disable and the clock sampling registers and holds them in the reset state until the synchronizing flip-flop output returns to its high state. When general control 1002 de-asserts signal 1012, synchronizing flip-flop 1036 is set on the next falling edge of data line 1025. The disable and clock sampling registers are no longer held in their reset states. On the next rising edge on data line 1025, the state of system clock 1010 is registered in system clock sampling flip-flop 1018 and sampling disable flip-flop 1014 is set to disable further changes in the state of flip-flop 1018 until it is reset in preparation to take another reading. The rising edge on 1025 propagates through delay 1022 and after a short delay appears at tap 1026. The rising edge at 1026 clocks the state of the system clock 1010 into system clock sampling flip-flop 1019 which is associated with tap 1026 and its associated sampling disable flip-flop 1015 is set. In a similar fashion, when the rising edge propagates from 1026 through delay element 1023 to tap 1027, system clock sampling flip-flop 1020 is set to the state of system clock 1010 and sampling disable flip-flop 1016 is set. The analogous process occurs for delay segment 1024, for system clock flip-flop 1021 and for sampling disable flip-flop 1017. With more delay line taps and associated sampling and sampling disable flip-flops, the pattern described above continues.

Interface general control 1002 momentarily issues the reset 1012 and may read the sampling disable register outputs on bus 1013 to determine when the flip-flops 1014 through 1017 are all set indicating that a reading has been taken. The system clock sampling register flip-flops 1018 through 1021 are then read on bus 1009. In the following it is assumed that there is one system clock cycle per received data bit, that the clock has a nominal duty cycle of 50%, and that the data input should be sampled a little after the midpoint of the period for which the data is stable. As an illustrative example, assume that a reading has been taken for which the outputs of system clock sampling flip-flops 1018 and 1019 are one and the outputs of system clock sampling flip-flops 1020 and 1021 are zero. For this case, the interface control 1002 determines that input data should be sampled at tap 1027 so that the data transitions take place, nominally, very shortly after the negative transition of the system clock. The positive transition of the 50% duty cycle system clock will then occur just after the halfway point of the bit period of the data sampled at tap 1027. Thus, the data should be sampled on the positive transition of the system clock. To set received data variable delay select 1029 to select tap 1027, the control interface outputs the appropriate select command on bus 1008 and registers the select command by pulsing line 1007. Flip-flop 1031 samples input data 1030 from the selected tap on the negative edge of the system clock and flip-flop 1033, depending on the setting of control line 1006, samples either the data sampled by 1031 or the data 1030 from the selected tap on the positive edge of the system clock. In either event, the received data on line 1034 is clocked in on the positive system clock. When control line 1006 is high, the data is sampled directly, and when control line 1006 is low, the data is sampled on the negative clock edge by 1031 and delayed by one half bit period before being clock into flip-flop 1033 on the rising edge of the system clock. Thus, to select sampling of the data on the positive transition of the system clock as required in the example, line 1006 is held high by interface control 1002. The interface receive block 1005 in combination with an interface general control block 1002 receive the extracted bit stream 1034 and after possible processing of the extracted input data 1034, data framing is done to separate data from idling periods and to properly interpret the input data and to direct it to the proper recipient.

Turning to FIG. 11, is a block diagram of a system that incorporates principles of this invention and which emphasizes the clock and data relationships within the system is shown. Data with the embedded clock reference is sent from interface unit 1100 to remote unit 1150 and data is returned in a phase synchronous format by remote unit 1150 to the interface unit 1100 where it is received and decoded.

The system clock 1104 in the interface unit preferably serves as the frequency reference for the entire system. It optionally but preferably includes frequency dithering to distribute radiated interference over wider frequency ranges cutting the amplitude of peak radiated emissions from the system. In block 1102, the system clock 1104 is used as a reference to encode data to send from block 1101. The transmitted data signal includes embedded clocking information. This encoded data stream is transmitted by interface line driver block 1103. In the remote unit 1150, information transmitted from interface unit 1100 is received by remote line receiver block 1151. In block 1152, the reference clock is extracted from the data stream. This reference clock is preferably multiplied to a higher frequency preferably using delay line elements in block 1153 and the multiplied clock frequency is preferably used as the clock for many or all of the blocks in the remote unit 1150. For example, the reference clock and the multiplied reference clock are preferably used to generate signals for use in extraction of the received data in block 1154.

The clock derived from the input data stream is used in block 1156 to encode remote data to send from block 1155 to the interface unit 1100. The remote line driver 1157 transmits the data from the remote unit to the interface unit where it is received by line receiver 1108. In block 1105, the received data is sampled and its phase is compared with the system clock 1104 or a phase synchronized derivative thereof and a determination is made to correctly adjust the phase preferably of the received data but optionally of the interface clock signal or of each to bring them into a phase relationship which is satisfactory for decoding of the data. The data which is received from the remote unit is decoded in block 1106. Note that, in the preferred design, the system clock 1104 serves directly or indirectly as the timing reference for all of the data transmit and data receive processes. It is for this reason that the data received from the remote unit by the interface unit is already in a relatively stable phase relation with a system clock 1104 so that periodic phase corrections are all that are required to use the system clock 1104 as the reference clock to decode the data received from remote unit 1150. Furthermore, when timing requirements are not too stringent, this phase relation may in some cases be satisfactorily established by design or in others by initial adjustment in production.

Figure 12:
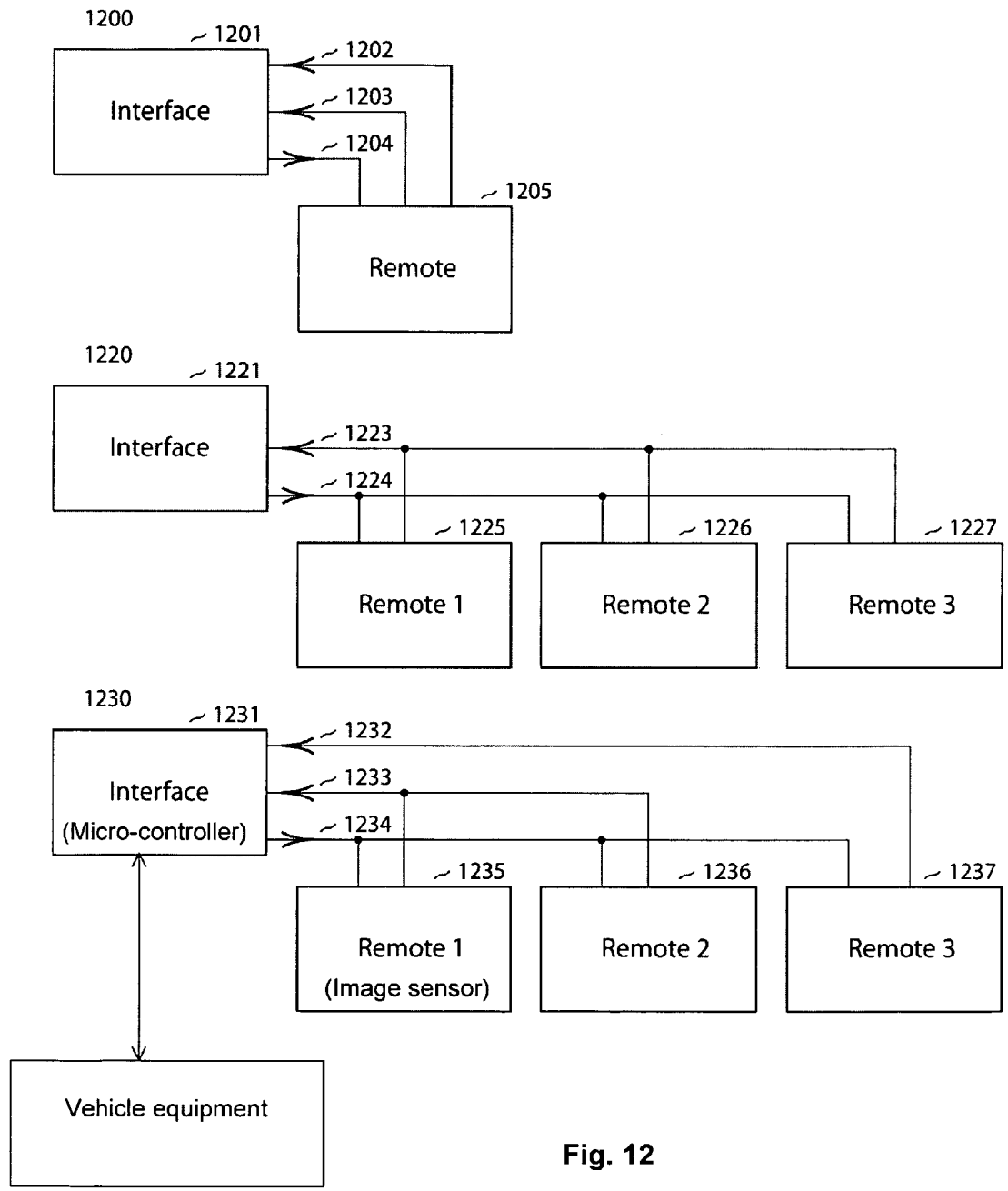
FIG. 12 depicts a diagram having various combinations of remote units and send and receive paths.

The separation of the send and receive data paths between interface unit and a remote unit or units makes it possible to use straightforward extensions of the design to incorporate such features as multiple return data paths to increase data handling capacity. This is illustrated by the interface unit 1201 and the remote unit 1205 in block 1200 of FIG. 12. Here instructions are sent from the interface unit 1201 over bus 1204 to the remote unit 1205 and data is returned from remote unit 1205 to interface unit 1201 over the dual paths 1202 and 1203.

In the final two illustrations 1220 and 1230, multiple remote units are attached to each of the interface units. In each of these cases, it is presumed that an address field is incorporated in the instructions sent from the interface units to the remotes so that it is possible to direct instructions to a specific remote unit. The address field may also include options to select all units for certain broadcast instructions or to select subgroups of the remote units. In some cases as with bus 1223 of arrangement 1220 and with bus 1233 of arrangement 1230, a bus is shared by more than one remote unit. In these cases, it is presumed that only one of the units on the bus requires the bus at a time or that the bus is time shared by some multiplexing scheme as known in the art and that the units have the capability to disconnect from the bus or otherwise go into a high impedance or other non-interfering state so that they do not interfere with transmissions from another unit when it is using the bus. In arrangement 1220, interface unit 1221 sends instructions over bus 1224 to the three remote units 1225, 1226, and 1227. The remote units share and return data on the bus 1223.

In arrangement 1230, interface unit 1231 sends instructions over bus 1234 to the three remote units 1235, 1236, and 1237. Here remote units 1235 and 1236 share bus 1233 to return data to the interface unit 1231. Remote unit 1237 returns data on bus 1232. In some cases, specialized independent or semi independent units may receive returned data so that data may not in all cases be returned directly to the interface unit. In such cases when the common clock reference is used, a mechanism must be provided to communicate the clock reference to units which require it. Also, phase relationships for the returned data may be different between given units. Because it may only be necessary to occasionally measure the phase, many embodiments of the invention may incorporate a common phase measuring device to measure the phase of the data returned from each of the remote units to the interface unit. The interface unit may in some cases provide separate phase synchronization devices for each or for a subgroup of the remote units and/or it may memorize the required phase corrections settings and set the phase corrections settings to receive data from a particular remote unit when the unit is returning data to the interface.

Although the present invention has been described with regard to specific embodiments, it should be understood that the scope of the present invention extends to all embodiments encompassed within the doctrine of equivalents.

What is claimed is:

1. An apparatus, comprising:
    at least one micro-controller;
    at least one digital serial communication link comprising a signal having encoding that is transition specific; and
    at least one image sensor in communication with said micro-controller via said digital serial communications link; and
    said signal comprising only one signal state change per transmitted bit.

2. An apparatus, comprising:
    at least one interface unit;
    at least one digital serial communication link comprising a first electronic signal comprising only one signal state change per transmitted bit, said first electronic signal comprising encoding that is transition specific;
    at least one remote unit in communication with said interface unit via said digital serial communications link; and
    a second electronic signal different from said first electronic signal, wherein one of said first electronic signal and said second electronic signal is employed to send data from said interface unit to said remote unit and the other one of said first electronic signal and said second electronic signal is employed to send data from said remote unit to said interface unit.

3. An apparatus as in claim 2 wherein said interface unit comprises a micro-controller.

4. An apparatus as in claim 3 wherein said remote unit comprises a micro-controller.

5. An apparatus as in claim 2 wherein said remote unit comprises an image sensor.

6. An apparatus as in claim 2 wherein transmissions from said interface unit to said remote unit comprises a lower or equal baud rate compared to transmissions from said remote unit to said interface unit.

7. An apparatus as in claim 2 wherein said second electronic signal comprises a protocol selected from the group comprising: RS-232, IEEE 1394-1995, IEEE-1395, MOST, CAN and AMI-C.

* * * * *

UNITED STATES PATENT AND TRADEMARK OFFICE
CERTIFICATE OF CORRECTION

PATENT NO. : 7,405,650 B2
APPLICATION NO. : 11/017128
DATED : July 29, 2008
INVENTOR(S) : Jeremy C. Andrus et al.

It is certified that error appears in the above-identified patent and that said Letters Patent is hereby corrected as shown below:

*Column 1, line 26, "one zero" should be -- one-zero --.
*Column 4, line 64, "these" should be -- there --.
*Column 4, line 65, "there in" should be -- therein --.
*Column 5, line 66, "vise" should be -- visa --.
*Column 8, line 22, "the" should be -- be --.
*Column 8, line 37, after "reset" delete "the".
*Column 8, line 37, "a" should be -- the --.
*Column 9, line 31, "generated" should be -- generate --.
*Column 9, line 37, "one zero" should be -- one-zero --.
*Column 10, line 1, after "absence" add -- of --.
*Column 14, line 66, "used for gigablt" should be -- use for gigabyte --.
*Column 16, lines 11 and 14, "signal's" should be -- signals --.
*Column 20, line 31, "calibrated" should be -- calibrate --.
*Column 21, line 39, "enabled" should be -- enable --.
*Column 21, line 50, "an" should be -- and --.
*Column 22, line 54, "Resisters" should be -- Resistors --.
*Column 22, lines 57 and 59, "resisters" should be -- resistors --.
*Column 23, line 38, "the" should be -- be --.
*Column 23, lines 43-44, "implementation's" should be -- implementation --.
*Column 24, line 3, after "utilizes" delete ",".
*Column 27, line 53, "clock" should be -- clocked --.

Signed and Sealed this

Second Day of March, 2010

David J. Kappos
*Director of the United States Patent and Trademark Office*